(12) United States Patent
Zhang et al.

(10) Patent No.: US 10,675,471 B2
(45) Date of Patent: Jun. 9, 2020

(54) ANTI-TACHYCARDIA PACING CONTROL IN AN IMPLANTABLE MEDICAL DEVICE SYSTEM

(71) Applicant: Medtronic, Inc., Minneapolis, MN (US)

(72) Inventors: Xusheng Zhang, Shoreview, MN (US); Yanina Grinberg, Plymouth, MN (US); Paul R. Solheim, Blaine, MN (US); Troy E. Jackson, Rogers, MN (US); Timothy A. Ebeling, Circle Pines, MN (US); Vladimir P. Nikolski, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 101 days.

(21) Appl. No.: 15/677,204

(22) Filed: Aug. 15, 2017

(65) Prior Publication Data

US 2019/0054297 A1 Feb. 21, 2019

(51) Int. Cl.
| | |
|---|---|
| *A61N 1/362* | (2006.01) |
| *A61N 1/39* | (2006.01) |
| *A61N 1/365* | (2006.01) |
| *A61N 1/372* | (2006.01) |
| *A61N 1/375* | (2006.01) |

(52) U.S. Cl.
CPC ......... *A61N 1/3622* (2013.01); *A61N 1/3624* (2013.01); *A61N 1/36507* (2013.01); *A61N 1/37217* (2013.01); *A61N 1/3987* (2013.01); *A61N 1/39622* (2017.08); *A61N 1/3756* (2013.01); *A61N 1/37512* (2017.08); *A61N 1/3918* (2013.01)

(58) Field of Classification Search
CPC ...... A61N 1/36; A61N 1/3622; A61N 1/3624; A61N 1/36507; A61N 1/37217; A61N 1/37512; A61N 1/3756; A61N 1/39622; A61N 1/3987
See application file for complete search history.

(56) References Cited

U.S. PATENT DOCUMENTS

| | | | |
|---|---|---|---|
| 5,987,356 A | * | 11/1999 | DeGroot .............. A61N 1/3622 607/5 |
| 6,393,316 B1 | | 5/2002 | Gillberg et al. |
| 6,721,597 B1 | | 4/2004 | Bardy et al. |

(Continued)

FOREIGN PATENT DOCUMENTS

EP 2459275 A1 6/2012

OTHER PUBLICATIONS

Zhang et al., "System and Method for Sensing and Detection in an Extra-Cardiovascular Implantable Cardioverter Defibrillator", U.S. Appl. No. 15/140,802, filed Apr. 28, 2016, 77 pages.

(Continued)

*Primary Examiner* — Christopher A Flory

(57) ABSTRACT

An implantable medical device system is configured to detect a tachyarrhythmia from a cardiac electrical signal and start an ATP therapy delay period. The implantable medical device determines whether the cardiac electrical signal received during the ATP therapy delay period satisfies ATP delivery criteria. A therapy delivery module is controlled to cancel the delayed ATP therapy if the ATP delivery criteria are not met and deliver the delayed ATP therapy if the ATP delivery criteria are met.

38 Claims, 17 Drawing Sheets

(56) References Cited

U.S. PATENT DOCUMENTS

| | | |
|---|---|---|
| 6,754,528 B2 | 6/2004 | Bardy et al. |
| 7,031,771 B2 | 4/2006 | Brown et al. |
| 7,212,855 B1 | 5/2007 | Kroll et al. |
| 7,761,150 B2 | 7/2010 | Ghanem et al. |
| 7,930,024 B2 | 4/2011 | Ousdigian |
| 8,160,684 B2 | 4/2012 | Ghanem et al. |
| 8,160,697 B2 | 4/2012 | Warren et al. |
| 8,195,291 B2 | 6/2012 | Norton et al. |
| 8,229,563 B2 | 7/2012 | Warren et al. |
| 8,249,702 B2 | 8/2012 | Warren et al. |
| 8,437,842 B2 | 5/2013 | Zhang et al. |
| 8,594,786 B2 | 11/2013 | Ousdigian |
| 8,670,826 B2 | 3/2014 | Warren et al. |
| 8,744,572 B1 | 6/2014 | Greenhut et al. |
| 8,825,145 B1 | 9/2014 | Zhang |
| 8,983,586 B2 | 3/2015 | Zhang |
| 8,996,101 B2 | 3/2015 | Zhang et al. |
| 9,002,443 B2 | 4/2015 | Zhang et al. |
| 9,031,649 B2 | 5/2015 | Ousdigian |
| 9,072,914 B2 | 7/2015 | Greenhut et al. |
| 9,149,645 B2 | 10/2015 | Sanghera et al. |
| 9,421,390 B2 | 8/2016 | Allavatam et al. |
| 9,468,766 B2 | 10/2016 | Sheldon et al. |
| 9,597,525 B2 | 3/2017 | Cao et al. |
| 9,669,224 B2 | 6/2017 | Carney et al. |
| 9,795,789 B2 | 10/2017 | Kaiser |
| 2007/0100380 A1* | 5/2007 | Fukui .......... A61N 1/3622 607/4 |
| 2008/0183228 A1* | 7/2008 | Kim .......... A61B 5/0452 607/4 |
| 2010/0198293 A1* | 8/2010 | Kaiser .......... A61N 1/3622 607/17 |
| 2010/0331904 A1* | 12/2010 | Warren .......... A61B 5/0464 607/5 |
| 2012/0071944 A1* | 3/2012 | Gunderson .......... A61N 1/3622 607/25 |
| 2012/0109240 A1 | 5/2012 | Zhou et al. |
| 2012/0303084 A1* | 11/2012 | Kleckner .......... A61N 1/36114 607/25 |
| 2012/0316613 A1 | 12/2012 | Keefe et al. |
| 2014/0100623 A1* | 4/2014 | Mitrani .......... A61B 5/0408 607/7 |
| 2014/0214104 A1* | 7/2014 | Greenhut .......... A61N 1/37288 607/4 |
| 2014/0276159 A1 | 9/2014 | Zhang |
| 2014/0330327 A1 | 11/2014 | Thompson-Nauman et al. |
| 2015/0290467 A1 | 10/2015 | Ludwig |
| 2015/0297905 A1* | 10/2015 | Greenhut .......... A61N 1/37288 607/4 |
| 2015/0305642 A1 | 10/2015 | Reinke et al. |
| 2015/0306375 A1 | 10/2015 | Marshall et al. |
| 2015/0306410 A1 | 10/2015 | Marshall et al. |
| 2015/0321011 A1* | 11/2015 | Carney .......... A61N 1/36514 607/62 |
| 2015/0360041 A1 | 12/2015 | Stahmann et al. |
| 2015/0375004 A1* | 12/2015 | Warren .......... A61B 5/0464 607/6 |
| 2016/0113534 A1* | 4/2016 | Cao .......... A61B 5/046 600/510 |
| 2016/0113537 A1* | 4/2016 | Cao .......... A61B 5/04012 600/510 |
| 2016/0113577 A1* | 4/2016 | Cao .......... A61B 5/04012 600/510 |
| 2016/0158567 A1 | 6/2016 | Marshall et al. |
| 2016/0228718 A1 | 8/2016 | Koop |
| 2017/0043173 A1* | 2/2017 | Sharma .......... A61N 1/3756 |
| 2017/0043174 A1* | 2/2017 | Greenhut .......... A61N 1/37288 |
| 2017/0157399 A1 | 6/2017 | Anderson et al. |
| 2017/0157413 A1 | 6/2017 | Anderson et al. |

OTHER PUBLICATIONS

Cao et al., "Multi-Threshold Sensing of Cardiac Electrical Signals in an Extracardiovascular Implantable Cardioverter Defibrillator", U.S. Appl. No. 15/142,171, filed Apr. 29, 2016, 71 pages.

Grinberg et al., "Asystole Detection and Response in an Implantable Cardioverter Defibrillator", U.S. Appl. No. 15/142,074, filed Apr. 29, 2016, 89 pages.

Zhang et al., "Cardiac Electrical Signal Gross Morphology-Based Noise Detection for Rejection of Ventricular Tachyarrhythmia Detection", U.S. Appl. No. 15/606,299, filed May 26, 2017, 98 pages.

Zhang, et al., "Detection of Electromagnetic Interference in a Cardiac Electrical Signal by an Implantable Medical Device", U.S. Appl. No. 15/416,827, filed Jan. 26, 2017, 106 pages.

Zhang, "Noise Detection and Frequency Determination in an Extra-Cardiovascular Implantable Cardioverter Defibrillator System", U.S. Appl. No. 15/416,461, filed Jan. 26, 2017, 64 pages.

Greenhut et al., "Caridac Electrical Signal Noise Detection for Tachyarrhythmia Episode Rejection", U.S. Appl. No. 15/606,216, filed May 26, 2017, 101 pages.

(PCT/US2018/045898) PCT Notification of Transmittal of the International Search Report and the Written Opinion of the International Searching Authority, dated Dec. 4, 2018, 10 pages.

* cited by examiner

ANTI-TACHYCARDIA PACING CONTROL IN AN IMPLANTABLE MEDICAL DEVICE SYSTEM

TECHNICAL FIELD

The disclosure relates generally to an implantable medical device system and method for delaying anti-tachycardia pacing (ATP) therapy and determining whether to deliver or cancel the delayed ATP therapy based on ATP delivery criteria.

BACKGROUND

Medical devices, such as cardiac pacemakers and ICDs, provide therapeutic electrical stimulation to a heart of a patient via electrodes carried by one or more medical electrical leads and/or electrodes on a housing of the medical device. The electrical stimulation may include signals such as pacing pulses or cardioversion or defibrillation shocks. In some cases, a medical device may sense cardiac electrical signals attendant to the intrinsic or pacing-evoked depolarizations of the heart and control delivery of stimulation signals to the heart based on sensed cardiac electrical signals. Upon detection of an abnormal rhythm, such as bradycardia, tachycardia or fibrillation, an appropriate electrical stimulation signal or signals may be delivered to restore or maintain a more normal rhythm of the heart. For example, an ICD may deliver pacing pulses to the heart of the patient upon detecting bradycardia or tachycardia or deliver cardioversion or defibrillation shocks to the heart upon detecting tachycardia or fibrillation. An extra-cardiovascular ICD system utilizes therapy delivery electrodes located outside the cardiovascular system, which avoids having to introduce implantable leads and electrodes within the patient's bloodstream. Electrical stimulation therapies that are delivered using extra-cardiovascular electrodes may require higher voltages in order to be effective compared to electrical stimulation therapies delivered using electrodes proximate to or in intimate contact with cardiac tissue, such as endocardial electrodes or epicardial electrodes.

SUMMARY

In general, the disclosure is directed to techniques for controlling delivery of ATP to a patient's heart by an implantable medical device system, which may include an extra-cardiovascular ICD in some examples. An implantable medical device system operating according to the techniques disclosed herein is configured to detect tachyarrhythmia and delay ATP therapy for a delay period. The system determines if a cardiac electrical signal satisfies ATP delivery criteria during the delay period and cancels the ATP therapy if the delivery criteria are unmet.

In one example, the disclosure provides an implantable medical device system including a sensing module configured to receive a cardiac electrical signal from a patient's heart and sense cardiac events from the cardiac electrical signal; a therapy delivery module configured to generate pulses for delivering an anti-tachycardia pacing (ATP) therapy to the patient's heart via a pacing electrode vector; and a control module coupled to the sensing module and the therapy delivery module. The control module is configured to detect a tachyarrhythmia from the cardiac electrical signal and start an ATP therapy delay period in response to detecting the tachyarrhythmia. The control module determines whether the cardiac electrical signal received by the sensing module during the ATP therapy delay period satisfies ATP delivery criteria and in response to the ATP delivery criteria being satisfied, controls the therapy delivery module to deliver the delayed ATP therapy. The control module cancels the delayed ATP therapy in response to the ATP delivery criteria not being met.

In another example, the disclosure provides a method performed by an implantable medical device system. The method includes detecting a tachyarrhythmia from a cardiac electrical signal and staring an ATP therapy delay period in response to detecting the tachyarrhythmia. The method further includes determining whether the cardiac electrical signal received during the ATP therapy delay period satisfies ATP delivery criteria, and in response to the ATP delivery criteria being satisfied, controlling a therapy delivery module to deliver the delayed ATP therapy. The method includes canceling the delayed ATP therapy in response to the ATP delivery criteria not being met.

In another example, the disclosure provides a non-transitory, computer-readable storage medium storing a set of instructions which, when executed by a control module of an implantable medical device system cause the system to detect a tachyarrhythmia from a cardiac electrical signal received by a sensing module from a patient's heart, and, in response to detecting the tachyarrhythmia, starting an ATP therapy delay period. The system is further caused to determine whether the cardiac electrical signal received by the sensing module during the ATP therapy delay period satisfies ATP delivery criteria and, in response to the ATP delivery criteria being satisfied, control a therapy delivery module to deliver the delayed ATP therapy. The instructions further cause the system to cancel the delayed ATP therapy in response to the ATP delivery criteria not being met.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In general, this disclosure describes techniques for controlling ATP delivery by an implantable medical device system. These techniques may be implemented in a variety of implantable medical device (IMD) systems capable of detecting tachyarrhythmia and generating and delivering electrical stimulation pulses for terminating the tachyarrhythmia, such as transvenous ICD systems, ICD systems that include an intra-cardiac pacemaker, and extra-cardiovascular ICD systems.

In some examples, the system includes an extra-cardiovascular ICD configured to deliver the ATP using implanted, extra-cardiovascular electrodes. As used herein, the term "extra-cardiovascular" refers to a position outside the blood vessels, heart, and pericardium surrounding the heart of a patient. Implantable electrodes carried by extra-cardiovascular leads may be positioned extra-thoracically (outside the ribcage and sternum) or intra-thoracically (beneath the ribcage or sternum) but generally not in intimate contact with myocardial tissue.

In IMD systems that include transvenous leads or an intra-cardiac pacemaker positioning pacing electrodes in contact or intimate proximity with myocardial tissue, a low voltage therapy module may deliver the ATP pacing pulses. Examples of IMD systems that may deliver ATP therapy using a low voltage therapy module and according to the techniques disclosed herein are shown and described in conjunction with FIGS. 10 and 11.

In an extra-cardiovascular ICD system, ATP may be delivered from the LV therapy module or from a high voltage (HV) therapy module, particularly when pacing pulses delivered from the low voltage pacing circuit, which uses relatively lower voltage capacitors, do not capture the heart. Capture is achieved when the energy of a delivered pulse is greater than a capture threshold and causes a depolarization of the myocardial tissue, often referred to as an "evoked response." In extra-cardiovascular ICD systems, the HV therapy module used for delivering high voltage cardioversion/defibrillation (CV/DF) shocks may be required for delivering cardiac pacing pulses since the pacing capture threshold of an extra-cardiovascular pacing electrode vector may be higher than the pacing pulse energy available from a low voltage pacing therapy module. The HV therapy module of an ICD generally includes a HV capacitor that is chargeable to a shock voltage amplitude for delivering a shock pulse to cardiovert or defibrillate the heart. The HV capacitor may be charged to a pacing voltage amplitude that is less than the shock voltage amplitude for delivering ATP. In some examples, an ICD configured to control ATP therapy delivery according to the techniques disclosed herein may deliver ATP pulses via implanted extra-cardiovascular electrodes from a HV therapy module that is also used for delivering CV/DF shocks.

Figure 1A:
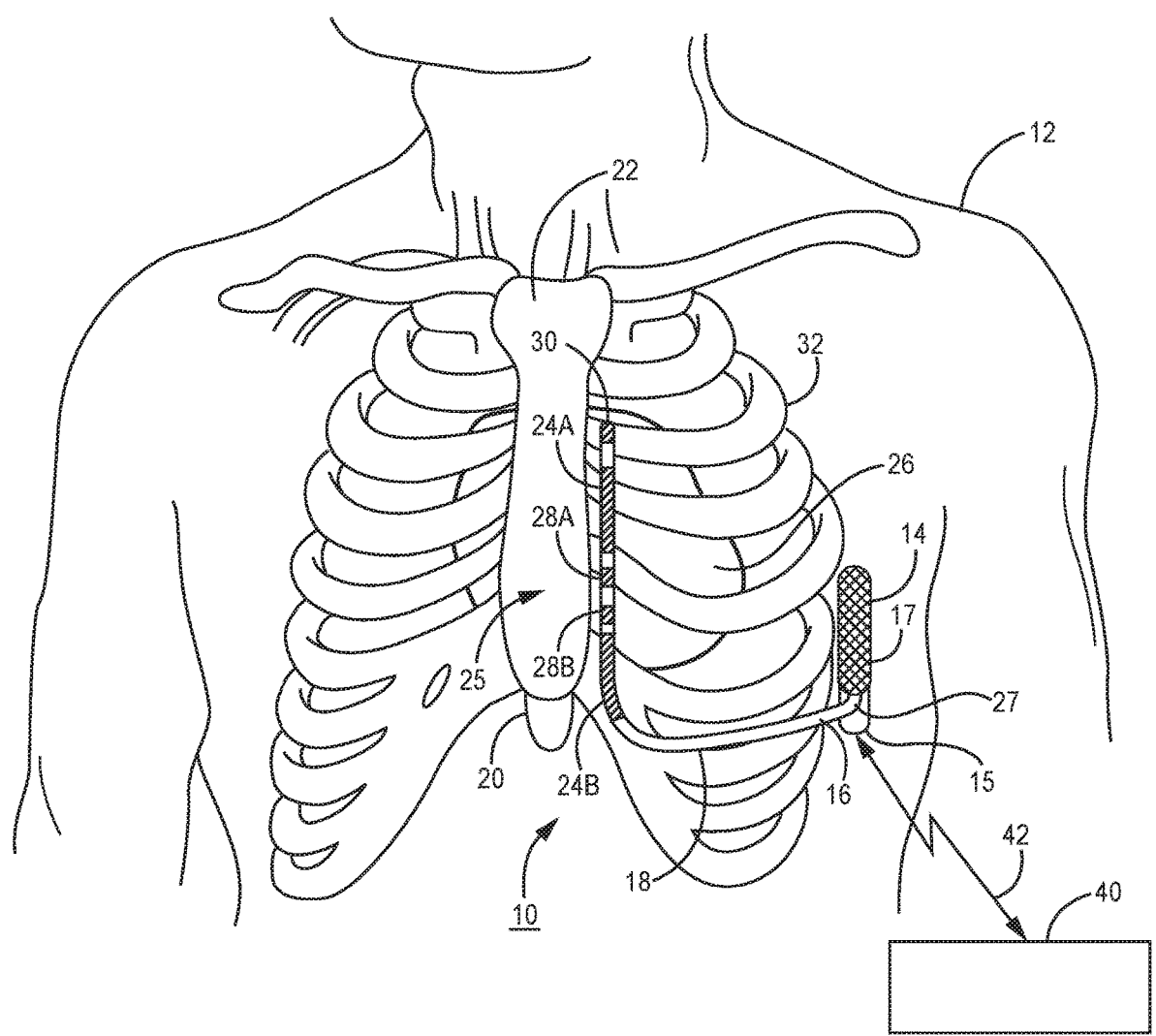
FIGS. 1A and 1B are conceptual diagrams of an extra-cardiovascular ICD system according to one example.
Figure 1B:
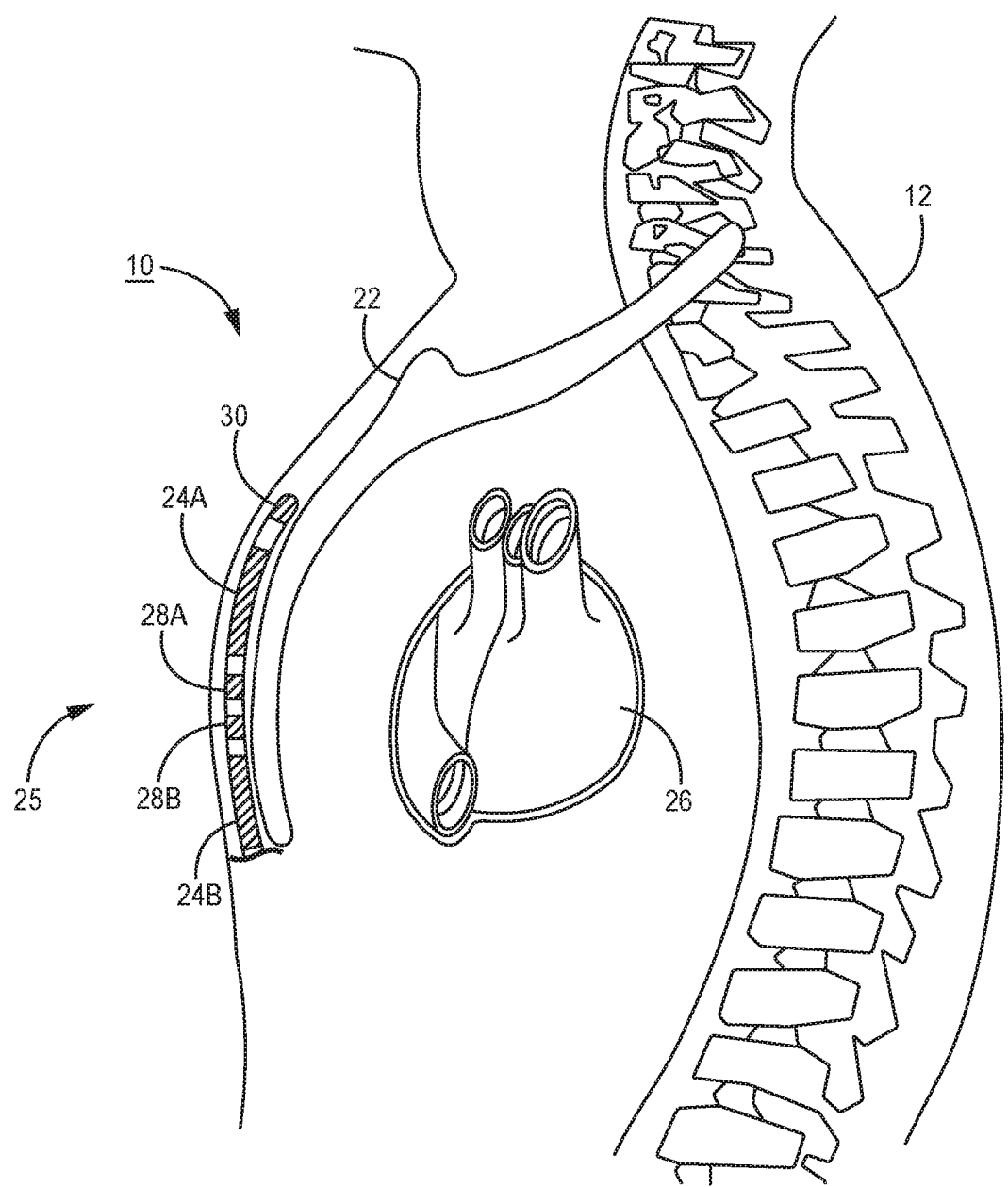

FIGS. 1A and 1B are conceptual diagrams of an extra-cardiovascular ICD system 10 according to one example. FIG. 1A is a front view of ICD system 10 implanted within patient 12. FIG. 1B is a side view of a portion of ICD system 10 implanted within patient 12. ICD system 10 includes an ICD 14 connected to an extra-cardiovascular electrical stimulation and sensing lead 16. FIGS. 1A and 1B are described in the context of an ICD system 10 capable of providing defibrillation and/or cardioversion shocks and cardiac pacing pulses.

ICD 14 includes a housing 15 that forms a hermetic seal that protects internal components of ICD 14. The housing 15 of ICD 14 may be formed of a conductive material, such as titanium or titanium alloy. The housing 15 may function as a housing electrode (sometimes referred to as a "can" electrode). In examples described herein, housing 15 may be used as an active can electrode for use in delivering high voltage CV/DF shocks and relatively lower voltage cardiac pacing pulses generated by a high voltage therapy module. The housing 15 of ICD 14 may include a plurality of electrodes on an outer portion of the housing instead of acting as a single electrode. The outer portion(s) of the housing 15 functioning as an electrode(s) may be coated with a material, such as titanium nitride, e.g., for reducing polarization artifact.

ICD 14 includes a connector assembly 17 (also referred to as a connector block or header) that includes electrical feedthroughs crossing housing 15 to provide electrical connections between conductors extending within an elongated lead body 18 of lead 16 and electronic components included within the housing 15 of ICD 14. As will be described in further detail herein, housing 15 may house one or more processors, memories, transceivers, sensors, electrical signal sensing circuitry, therapy delivery circuitry, power sources and other appropriate components.

Elongated lead body 18 includes a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead 16 includes defibrillation electrodes 24A and 24B, collectively 24, and pace/sense electrodes 28A, 28B, and 30. In some cases, defibrillation electrodes 24A and 24B may together form a defibrillation electrode in that they are configured to be activated concurrently. Alternatively, defibrillation electrodes 24A and 24B may form separate defibrillation electrodes in which case each of the electrodes 24A and 24B may be activated independently. In some instances, defibrillation electrodes 24A and 24B are coupled to electrically isolated conductors, and ICD 14 may include switching mechanisms to allow electrodes 24A and 24B to be utilized as a single defibrillation electrode (e.g., activated concurrently to form a common cathode or anode) or as separate defibrillation electrodes, (e.g., activated individually, one as a cathode and one as an anode or activated one at a time, one as an anode or cathode and the other remaining inactive with housing 15 as an active electrode).

Electrodes 24A and 24B (and in some example housing 15) are referred to as defibrillation electrodes because they are utilized, individually or collectively, for delivering high voltage stimulation shocks (e.g., cardioversion or defibrillation shocks). Electrodes 24A and 24B may be elongated coil electrodes and generally have a relatively high surface area for delivering high voltage electrical stimulation shocks compared to low voltage pacing and sensing electrodes. However, electrodes 24A and 24B and housing 15 may also be utilized to provide pacing functionality, sensing functionality or both pacing and sensing functionality in addition to or instead of high voltage shocks. In this sense, the use of the term "defibrillation electrode" herein should not be considered as limiting the electrodes 24A and 24B to use in only high voltage CV/DF shock delivery. As described herein, electrodes 24A and/or 24B may be used in a pacing electrode vector for delivering extra-cardiovascular pacing pulses from a high-voltage therapy module that is also used for delivering CV/DF shocks.

Electrodes 28A, 28B and 30 are relatively smaller surface area electrodes for delivering relatively low voltage pacing pulses and for sensing cardiac electrical signals. Electrodes 28A, 28B and 30 are referred to as pace/sense electrodes because they are generally configured for use in low voltage applications, e.g., used as either a cathode or anode for delivery of pacing pulses and/or sensing of cardiac electrical signals. In some instances, electrodes 28A, 28B, and 30 may provide only pacing functionality, only sensing functionality or both.

In the example illustrated in FIGS. 1A and 1B, electrodes 28A and 28B are located between defibrillation electrodes 24A and 24B and electrode 30 is located distal to defibrillation electrode 24A. Electrodes 28A and 28B are illustrated as ring electrodes, and electrode 30 is illustrated as a hemispherical tip electrode in the example of FIGS. 1A and 1B. However, electrodes 28A, 28B, and 30 may comprise any of a number of different types of electrodes, including ring electrodes, short coil electrodes, paddle electrodes, hemispherical electrodes, directional electrodes, segmented electrodes, or the like, and may be positioned at any position along the distal portion 25 of lead 16. Further, electrodes 28A, 28B, and 30 may be of similar type, shape, size and material or may differ from each other.

Lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superior subcutaneously or submuscularly over the ribcage and/or sternum, substantially parallel to sternum 22. Although illustrated in FIGS. 1A and 1B as being offset laterally from and extending substantially parallel to sternum 22, lead 16 may be implanted at other locations, such as over sternum 22, offset to the right or left of sternum 22, angled laterally from sternum 22 toward the left or the right, or the like. Alternatively, lead 16 may be placed along other subcutaneous or submuscular paths. The path of lead 16 may depend on the location of ICD 14 or other factors.

Electrical conductors (not illustrated) extend through one or more lumens of the elongated lead body 18 of lead 16 from the lead connector at the proximal lead end 27 to respective electrodes 24A, 24B, 28A, 28B, and 30 located along the distal portion 25 of the lead body 18. Lead body 18 may be tubular or cylindrical in shape. In other examples, the distal portion 25 (or all of) the elongated lead body 18 may have a flat, ribbon or paddle shape. The lead body 18 of lead 16 may be formed from a non-conductive material, including silicone, polyurethane, fluoropolymers, mixtures thereof, and other appropriate materials, and shaped to form one or more lumens within which the one or more conductors extend. However, the techniques disclosed herein are not limited to such constructions or to any particular lead body design.

The elongated electrical conductors contained within the lead body 18 electrically couple the electrodes 24A, 24B, 28A, 28B and 30 to circuitry, such as a therapy module and/or a sensing module, of ICD 14 via connections in the connector assembly 17, including associated electrical feedthroughs crossing housing 15. The electrical conductors transmit therapy from a therapy module within ICD 14 to one or more of defibrillation electrodes 24A and 24B and/or pace/sense electrodes 28A, 28B, and 30 and transmit sensed electrical signals from one or more of defibrillation electrodes 24A and 24B and/or pace/sense electrodes 28A, 28B, and 30 to the sensing module within ICD 14.

FIGS. 1A and 1B are illustrative in nature and should not be considered limiting of the practice of the techniques disclosed herein. In other examples, lead 16 may include less than three pace/sense electrodes or more than three pace/sense electrodes and/or a single defibrillation electrode or more than two electrically isolated or electrically coupled defibrillation electrodes or electrode segments. The pace/sense electrodes 28A, 28B, and 30 may be located elsewhere along the length of lead 16, e.g., distal to defibrillation electrode 24A, proximal to defibrillation electrode 24B, and/or between electrodes 24A and 24B. For example, lead 16 may include a single pace/sense electrode 28 between defibrillation electrodes 24A and 24B and no pace/sense electrode distal to defibrillation electrode 24A or proximal to defibrillation electrode 24B.

In other examples, lead 16 may include only a single pace/sense electrode 28 between defibrillation electrodes 24A and 24B and include another discrete electrode(s) distal to defibrillation electrode 24A and/or proximal to defibrillation electrode 24B. Various example configurations of extra-cardiovascular leads and electrodes and dimensions that may be implemented in conjunction with the extra-cardiovascular pacing techniques disclosed herein are described in commonly-assigned U.S. Pat. Publication No. 2015/0306375 (Marshall, et al.) and U.S. Pat. Publication No. 2015/0306410 (Marshall, et al.), both of which are incorporated herein by reference in their entirety.

In still other examples, ICD system 10 of FIGS. 1A and 1B may include a second extra-cardiovascular electrical stimulation and sensing lead similar to lead 16. The second lead may, for example, extend laterally to the posterior of patient 12 and include one or more electrodes that form an electrode vector with one or more of electrodes 24A, 24B, 28A, 28B, and/or 30 of lead 16 for providing cardiac pacing in accordance with the techniques disclosed herein.

ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferior from the manubrium to the desired location subcutaneously or submuscularly. In yet another example, ICD 14 may be placed abdominally. Lead 16 may be implanted in other extra-cardiovascular locations as well. For instance, as described with respect to FIGS. 2A-2C, the distal portion 25 of lead 16 may be implanted underneath the sternum/ribcage in the substernal space.

In some instances, electrodes 24A, 24B, 28A, 28B, and/or 30 of lead 16 may be shaped, oriented, designed or otherwise configured to reduce extra-cardiac stimulation. For example, electrodes 24A, 24B, 28A, 28B, and/or 30 of lead 16 may be shaped, oriented, designed, partially insulated or otherwise configured to focus, direct or point electrodes 24A, 24B, 28A, 28B, and/or 30 toward heart 26. In this manner, electrical stimulation pulses delivered via lead 16 are directed toward heart 26 and not outward toward skeletal muscle. For example, electrodes 24A, 24B, 28A, 28B, and/or 30 of lead 16 may be partially coated or masked with a polymer (e.g., polyurethane) or another coating material (e.g., tantalum pentoxide) on one side or in different regions so as to direct the electrical energy toward heart 26 and not outward toward skeletal muscle. In the case of a ring electrode, for example, the ring electrode may be partially coated with the polymer or other material to form a half-ring electrode, quarter-ring electrode, or other partial-ring electrode. When ICD 14 delivers pacing pulses via electrodes 24A, 24B, 28A, 28B, and/or 30, recruitment of surrounding skeletal muscle by the pacing pulses, which may cause discomfort to the patient, may be reduced by shaping, orienting, or partially insulating electrodes 24 to focus or direct electrical energy toward heart 26.

ICD 14 may obtain electrical signals corresponding to electrical activity of heart 26 via one or more sensing electrode vectors that include a combination of electrodes 28A, 28B, and 30 and the housing 15 of ICD 14. For example, ICD 14 may obtain cardiac electrical signals sensed using a sensing vector between combinations of electrodes 28A, 28B, and 30 with one another or obtain cardiac electrical signals using a sensing vector between any one or more of electrodes 28A, 28B, and 30 and the conductive housing 15 of ICD 14. In some instances, ICD 14 may even obtain cardiac electrical signals using a sensing vector that includes one or both defibrillation electrodes 24A or 24B such as between each other or in combination with one or more of electrodes 28A, 28B, and 30, and/or the housing 15.

ICD 14 analyzes the cardiac electrical signals received from one or more of the sensing vectors to monitor for abnormal rhythms, such as bradycardia, ventricular tachycardia (VT) or ventricular fibrillation (VF), for detecting a need for cardiac pacing or a CV/DF shock. ICD 14 may analyze the heart rate and/or morphology of the cardiac electrical signals to monitor for tachyarrhythmia in accordance with any of a number of tachyarrhythmia detection techniques. One example technique for detecting tachyarrhythmia is described in U.S. Pat. No. 7,761,150 (Ghanem, et al.), incorporated by reference herein in its entirety.

ICD 14 generates and delivers electrical stimulation therapy in response to detecting a tachyarrhythmia (e.g., VT or VF). ICD 14 may deliver one or more CV/DF shocks via one or both of defibrillation electrodes 24A and 24B and/or housing 15 if VT or VF is detected. In some therapy protocols anti-tachycardia pacing (ATP) pulses are delivered prior to a CV/DF shock in response to detecting VT or VF and may terminate the tachyarrhythmia, precluding the need for a shock.

ATP pulses may be delivered using an electrode vector that includes one or more of the electrodes 24A, 24B, 28A, 28B and/or 30, and/or the housing 15 of ICD 14. As described below, ICD 14 may be configured to deliver cardiac pacing pulses from a high voltage (HV) therapy module and may control the high voltage therapy module to deliver ATP after preparing the HV therapy module for delivering the ATP and confirming that ATP delivery criteria are met.

An external device 40 is shown in telemetric communication with ICD 14 by a communication link 42. External device 40 may include a processor, display, user interface, telemetry unit and other components for communicating with ICD 14 for transmitting and receiving data via communication link 42. Communication link 42 may be established between ICD 14 and external device 40 using a radio frequency (RF) link such as BLUETOOTH®, Wi-Fi, or Medical Implant Communication Service (MICS) or other RF or communication frequency bandwidth.

External device 40 may be embodied as a programmer used in a hospital, clinic or physician's office to retrieve data from ICD 14 and to program operating parameters and algorithms in ICD 14 for controlling ICD functions. External device 40 may be used to program cardiac rhythm detection parameters and therapy control parameters used by ICD 14. Control parameters used to generate and deliver cardiac electrical stimulation pulses according to techniques disclosed herein, including ATP protocols, may be programmed into ICD 14 using external device 40.

Data stored or acquired by ICD 14, including physiological signals or associated data derived therefrom, results of device diagnostics, and histories of detected rhythm episodes and delivered therapies, may be retrieved from ICD 14 by external device 40 following an interrogation command. For example, pacing capture threshold tests may be initiated by a user interacting with external device 40. A user may observe cardiac electrical signals retrieved from ICD 14 on a display of external device 40 for confirming cardiac capture by pacing pulses delivered by ICD 14 during a capture threshold test. External device 40 may alternatively be embodied as a home monitor or hand held device.

Figure 2A:
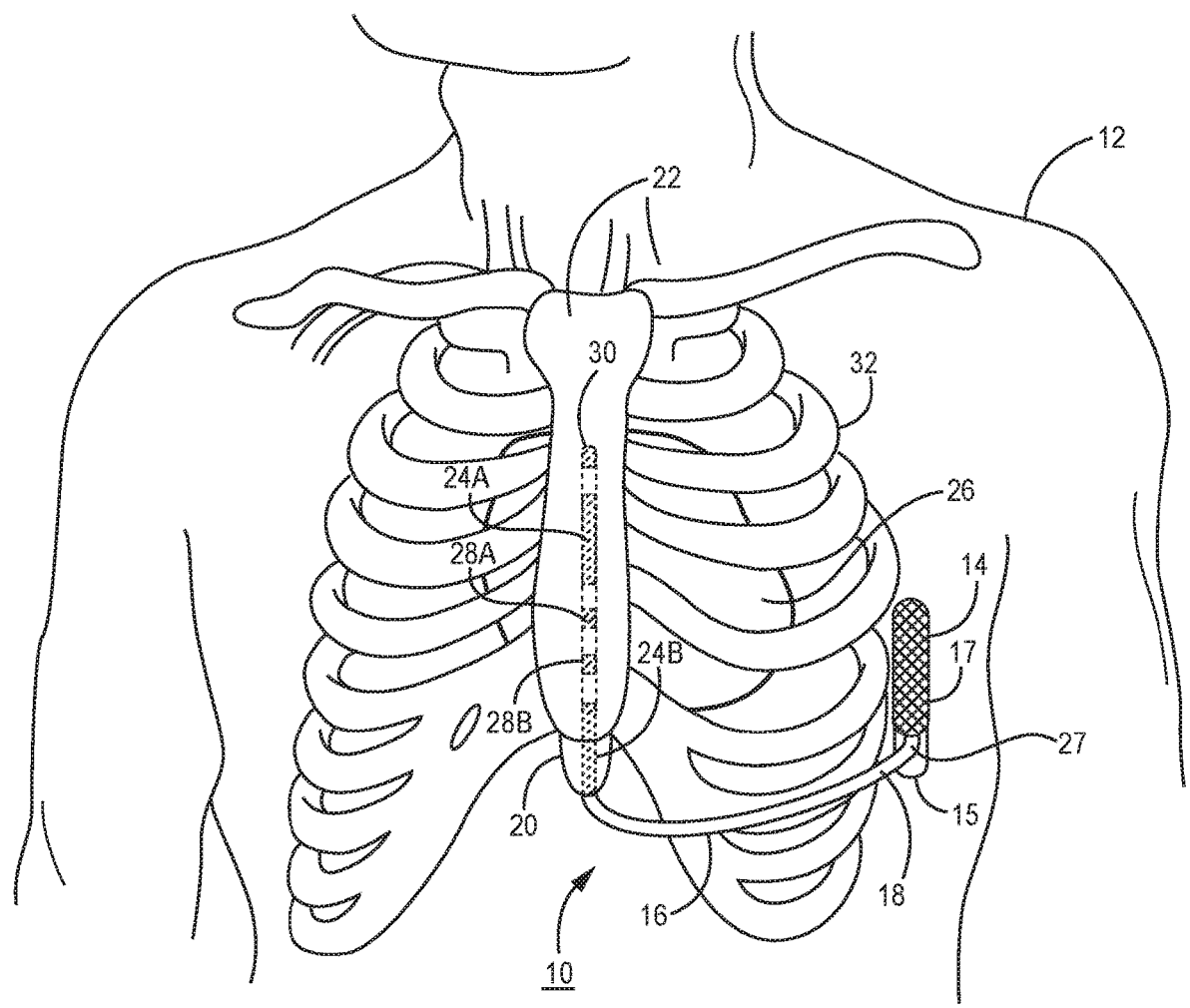
FIGS. 2A-2C are conceptual diagrams of a patient implanted with the extra-cardiovascular ICD system of FIG. 1A in a different implant configuration.
Figure 2B:
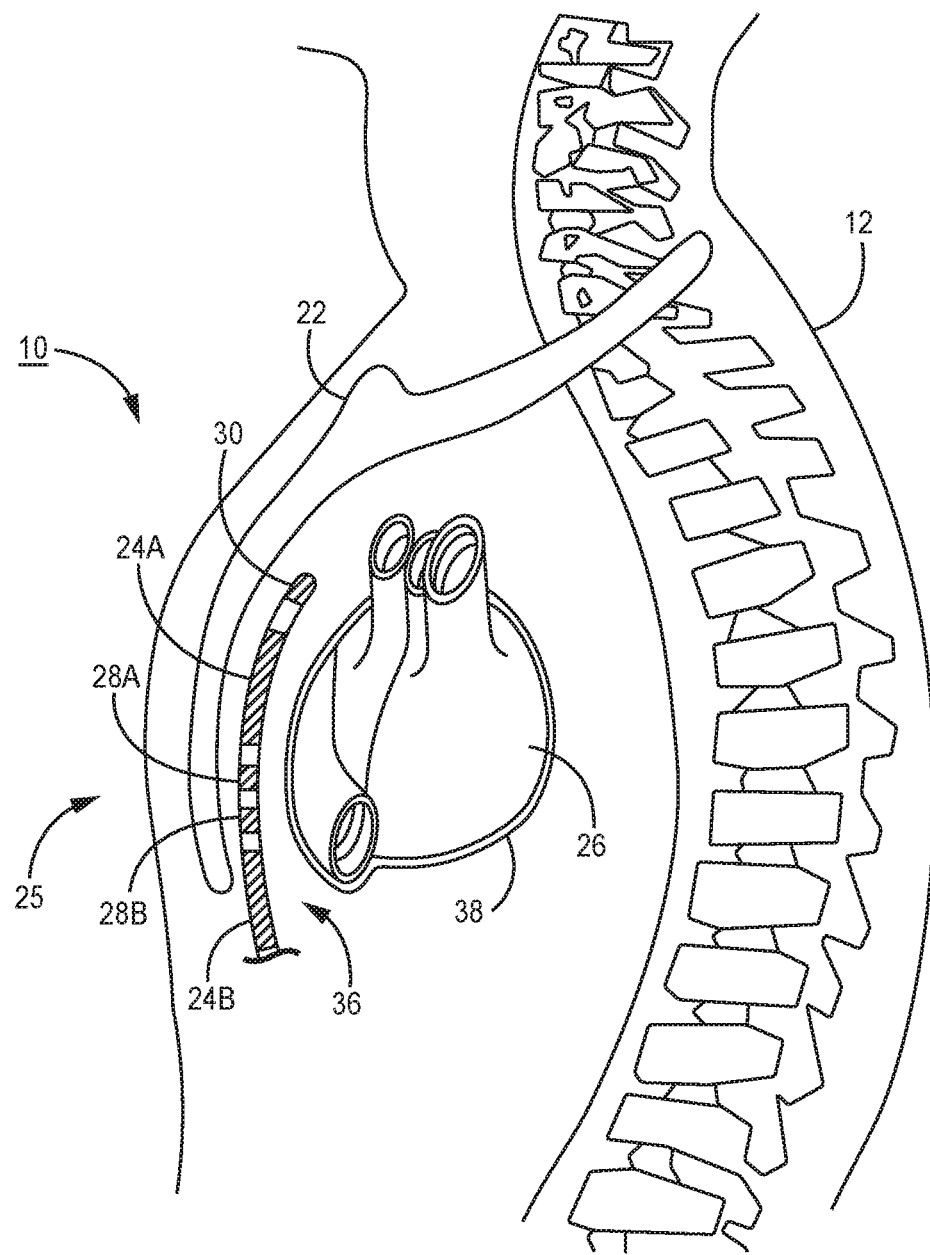
Figure 2C:
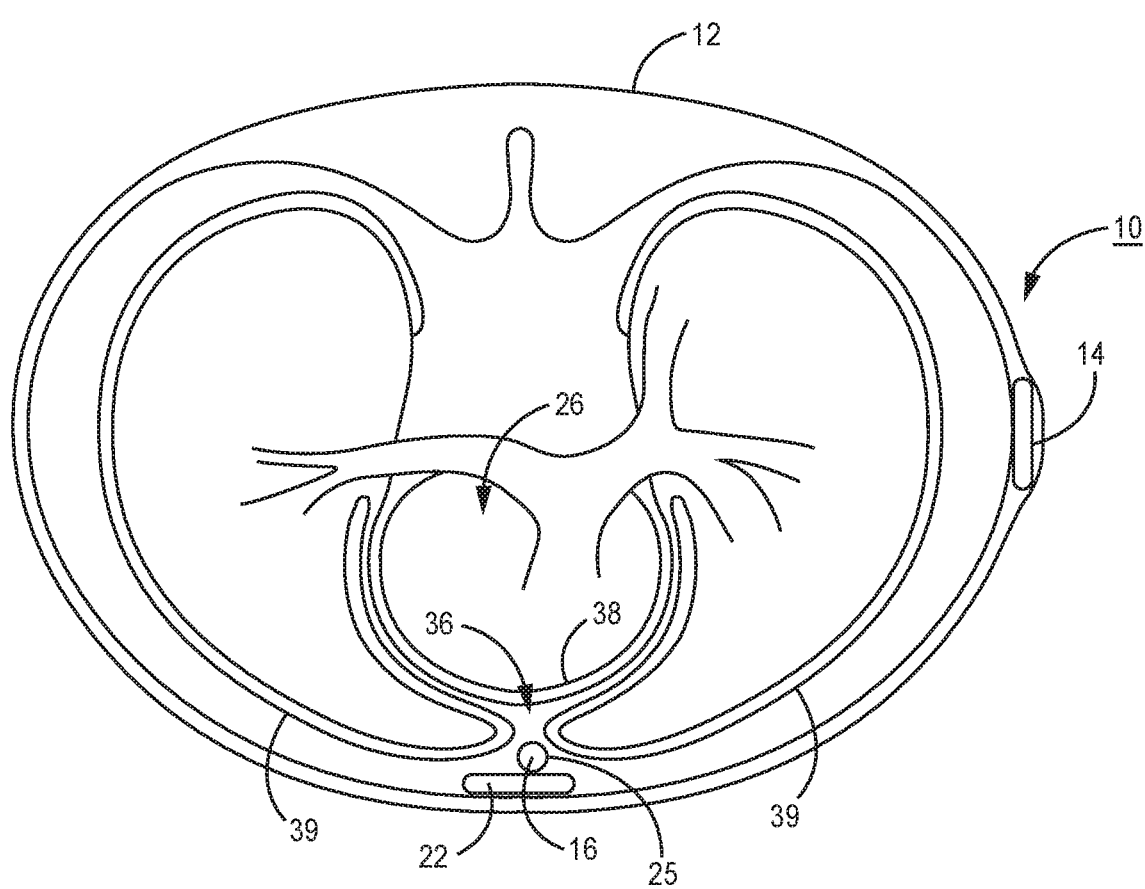

FIGS. 2A-2C are conceptual diagrams of patient 12 implanted with ICD system 10 in a different implant configuration than the arrangement shown in FIGS. 1A-1B. FIG. 2A is a front view of patient 12 implanted with ICD system 10. FIG. 2B is a side view of patient 12 implanted with ICD system 10. FIG. 2C is a transverse view of patient 12 implanted with ICD system 10. In this arrangement, lead 16 of system 10 is implanted at least partially underneath sternum 22 of patient 12. Lead 16 extends subcutaneously or submuscularly from ICD 14 toward xiphoid process 20 and at a location near xiphoid process 20 bends or turns and extends superiorly within anterior mediastinum 36 in a substernal position.

Anterior mediastinum 36 may be viewed as being bounded laterally by pleurae 39, posteriorly by pericardium 38, and anteriorly by sternum 22. In some instances, the anterior wall of anterior mediastinum 36 may also be formed by the transversus thoracis muscle and one or more costal cartilages. Anterior mediastinum 36 includes a quantity of loose connective tissue (such as areolar tissue), adipose tissue, some lymph vessels, lymph glands, substernal musculature, small side branches of the internal thoracic artery or vein, and the thymus gland. In one example, the distal portion 25 of lead 16 extends along the posterior side of sternum 22 substantially within the loose connective tissue and/or substernal musculature of anterior mediastinum 36.

A lead implanted such that the distal portion 25 is substantially within anterior mediastinum 36 may be referred to as a "substernal lead." In the example illustrated in FIGS. 2A-2C, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiovascular, intra-thoracic locations, including the pleural cavity or around the perimeter of and adjacent to but typically not within the pericardium 38 of heart 26. Other implant locations and lead and electrode arrangements that may be used in conjunction with the cardiac pacing techniques described herein are generally disclosed in the above-incorporated references. Although example extra-cardiovascular locations are described above with respect to FIGS. 1A, 1B and 2A-2C, the cardiac pacing techniques of this disclosure may be utilized in other implementations of extra-cardiovascular pacing applications.

Figure 3:
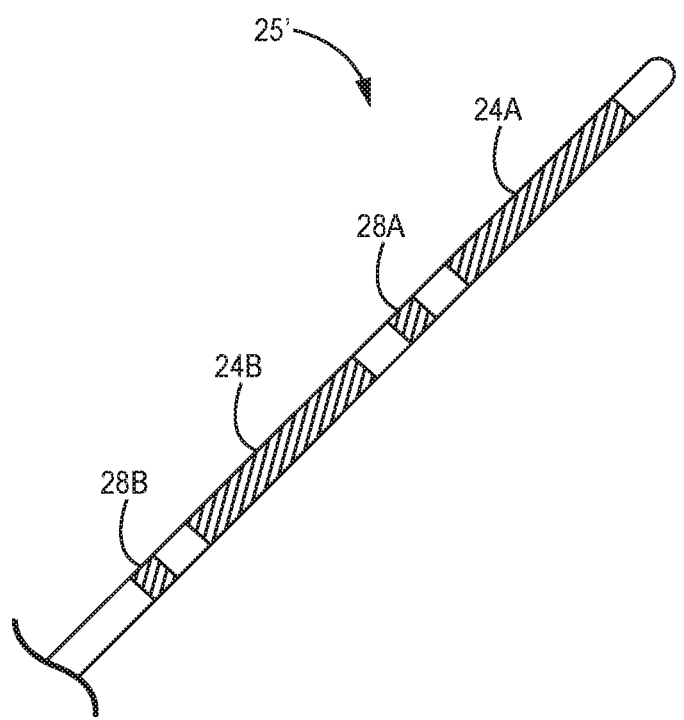
FIG. 3 is a conceptual diagram of a distal portion of an extra-cardiovascular lead having an electrode configuration according to another example.

FIG. 3 is a conceptual diagram illustrating a distal portion 25' of another example of implantable electrical lead 16 having an alternative electrode arrangement. In this example, distal portion 25' includes two pace/sense electrodes 28A and 28B and two defibrillation electrodes 24A and 24B and respective conductors (not shown) to provide the electrical stimulation and sensing functionality as described above in conjunction with FIGS. 1A, 1B and FIGS. 2A-2C. In this example, however, electrode 28B is proximal to proximal defibrillation electrode 24B, and electrode 28A is distal to proximal defibrillation electrode 24B such that electrodes 28A and 28B are separated by defibrillation electrode 24B. In a further example, in addition to electrodes 28A and 28B, lead 16 may include a third pace/sense electrode located distal to defibrillation electrode 24A.

The spacing and location of pace/sense electrodes 28A and 28B may be selected to provide pacing vectors that enable efficient pacing of heart 26. The lengths and spacing of electrodes 24A, 24B, 28A and 28B may correspond to any of the examples provided in the above-incorporated references. For example, the distal portion 25' of lead 16 from the distal end to the proximal side of the most proximal electrode (e.g., electrode 28B in the example of FIG. 3) may be less than or equal to 15 cm and may be less than or equal to 13 cm and or even less than or equal to 10 cm. The spacing and location of pace/sense electrodes 28A and 28B may be selected to provide pacing vectors that enable efficient pacing of heart 26. It is contemplated that one or more pace/sense electrodes may be distal to distal defibrillation electrode 24A, one or more pace/sense electrodes may be between defibrillation electrodes 24A and 24B, and/or one or more pace/sense electrodes may be proximal to proximal defibrillation electrode 24B. Having multiple pace/sense electrodes at different locations along lead body 18 enables selection from among a variety of inter-electrode spacings, which allows a pacing electrode pair (or combination) to be selected having an inter-electrode spacing that results in the greatest pacing efficiency.

ICD 14 may deliver electrical stimulation and/or sense electrical signals using any electrode vector that includes defibrillation electrodes 24A and 24B (individually or collectively), and/or electrodes 28A and/or 28B, and/or the housing 15 of ICD 14. As disclosed herein, ATP may be delivered from a HV therapy module in response to detecting a tachyarrhythmia. The ATP may be delivered via a pacing electrode vector selected from the extra-cardiovascular electrodes 24A, 24B, 28A, 28B, 30 and housing 15. The pacing electrode vector for ATP delivery from the HV therapy module may be between the defibrillation electrodes 24A and 24B, one as the anode and one as the cathode, or between one or both of defibrillation electrodes 24A and 24B as a cathode (or anode) and the housing 15 of ICD 14 as an anode (or cathode). In some cases, a pace/sense electrode 28A, 28B, and/or 30 may be included in a pacing electrode vector used to deliver ATP generated by the HV therapy module as described herein.

Figure 4:
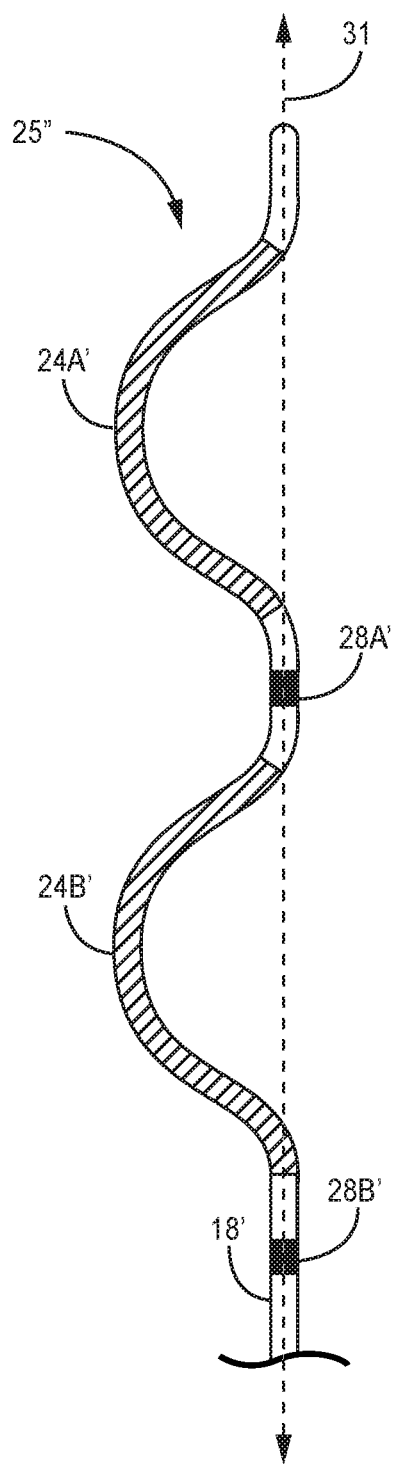
FIG. 4 is a conceptual diagram of a distal portion of an extra-cardiovascular lead having a lead body shape according to another example.

FIG. 4 is a conceptual diagram illustrating a distal portion 25" of another example of extra-cardiovascular lead 16 having an electrode arrangement similar to that of FIG. 3 but with a non-linear or curving distal portion 25" of lead body 18'. Lead body 18' may be pre-formed to have a normally curving, bending, serpentine, undulating, or zig-zagging shape along distal portion 25". In this example, defibrillation electrodes 24A' and 24B' are carried along pre-formed curving portions of the lead body 18'. Pace/sense electrode 28A' is carried between defibrillation electrodes 24A' and 24B'. Pace/sense electrode 28B' is carried proximal to the proximal defibrillation electrode 24B'.

In one example, lead body 18' may be formed having a normally curving distal portion 25" that includes two "C" shaped curves, which together may resemble the Greek letter epsilon, "ε." Defibrillation electrodes 24A' and 24B' are each carried by the two respective C-shaped portions of the lead body distal portion 25" and extend or curve in the same direction. In the example shown, pace/sense electrode 28A' is proximal to the C-shaped portion carrying electrode 24A', and pace/sense electrode 28B' is proximal to the C-shaped portion carrying electrode 24B'. Pace/sense electrodes 24A' and 24B' are approximately aligned with a central axis 31 of the normally straight or linear, proximal portion of lead body 18' such that mid-points of defibrillation electrodes 24A' and 24B' are laterally offset from electrodes 28A' and 28B'. Defibrillation electrodes 24A' and 24B' are located along respective C-shaped portions of the lead body distal portion 25" that extend laterally in the same direction away from central axis 31 and electrodes 28A' and 28B'. Other examples of extra-cardiovascular leads including one or more defibrillation electrodes and one or more pacing and sensing electrodes carried by curving serpentine, undulating or zig-zagging distal portion of the lead body that may be implemented with the pacing techniques described herein are generally disclosed in pending U.S. Pat. Publication No. 2016/0158567 (Marshall, et al.), incorporated herein by reference in its entirety.

Figure 5:
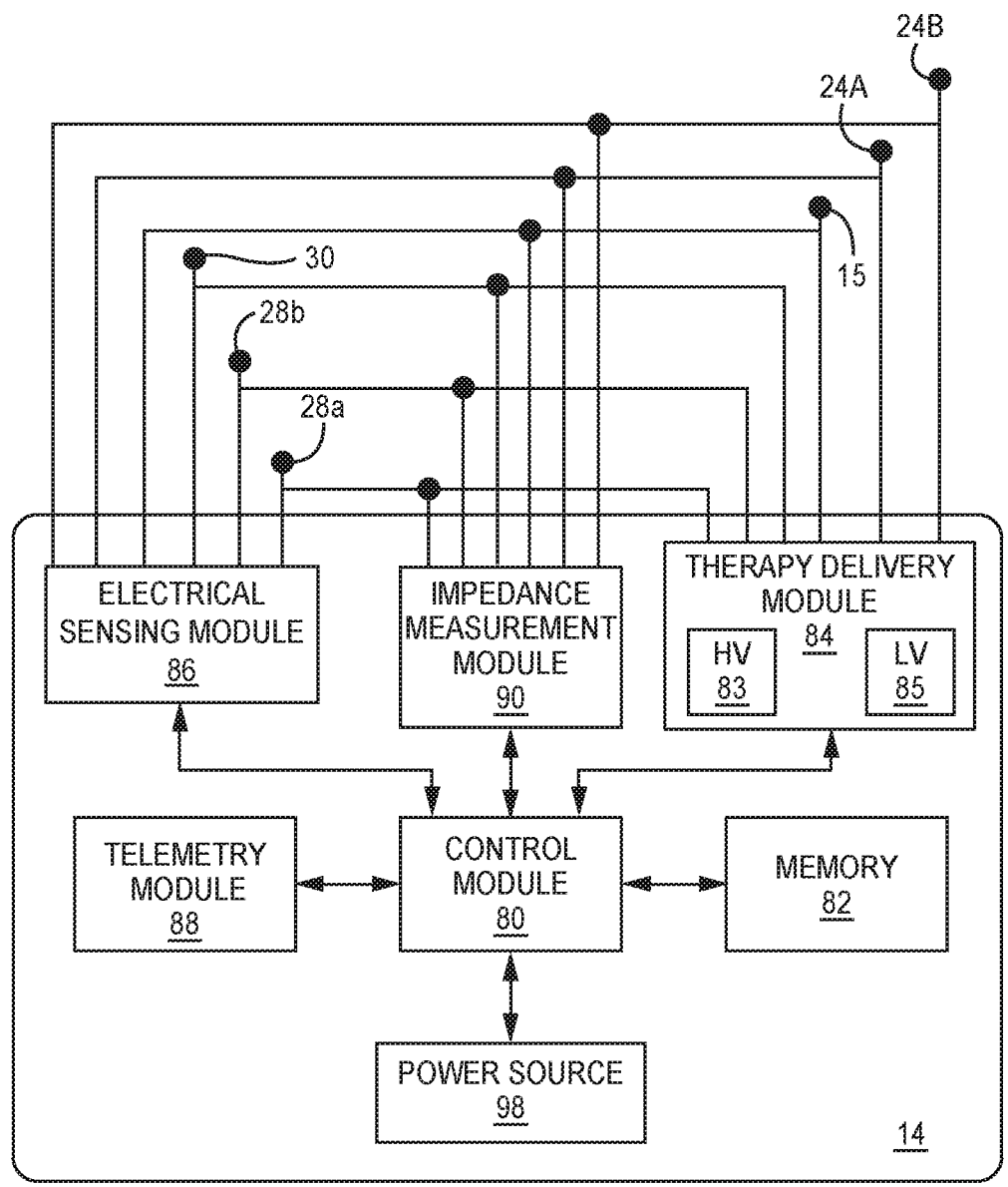
FIG. 5 is a schematic diagram of the ICD of the system of FIGS. 1A-2C according to one example.

FIG. 5 is a schematic diagram of ICD 14 according to one example. The electronic circuitry enclosed within housing 15 (shown schematically as a can electrode in FIG. 5) includes software, firmware and hardware that cooperatively monitor one or more cardiac electrical signals, determine when a pacing therapy is necessary, and deliver prescribed pacing therapies as needed. The software, firmware and hardware are also configured to determine when a CV/DF shock is necessary, and deliver prescribed CV/DF shock therapies. ICD 14 is coupled to an extra-cardiovascular lead, such as lead 16 carrying extra-cardiovascular electrodes 24A, 24B, 28A, 28B and 30, for delivering pacing therapies, CV/DF shock therapies and sensing cardiac electrical signals.

ICD 14 includes a control module 80, memory 82, therapy delivery module 84, electrical sensing module 86, and telemetry module 88. ICD 14 may include an impedance measurement module 90 for delivering a drive signal across a therapy delivery electrode vector and measuring a resulting voltage for determining an electrical impedance of the electrode vector.

A power source 98 provides power to the circuitry of ICD 14, including each of the modules 80, 82, 84, 86, 88, 90 as needed. Power source 98 may include one or more energy storage devices, such as one or more rechargeable or non-rechargeable batteries. The connections between power source 98 and each of the other modules 80, 82, 84, 86 and 88 are to be understood from the general block diagram of FIG. 3, but are not shown for the sake of clarity. For example, power source 98 is coupled to low voltage (LV) and HV charging circuits included in therapy delivery module 84 for charging LV and HV capacitors, respectively, or other energy storage devices included in therapy delivery module 84 for producing electrical stimulation pulses.

Figure 10:
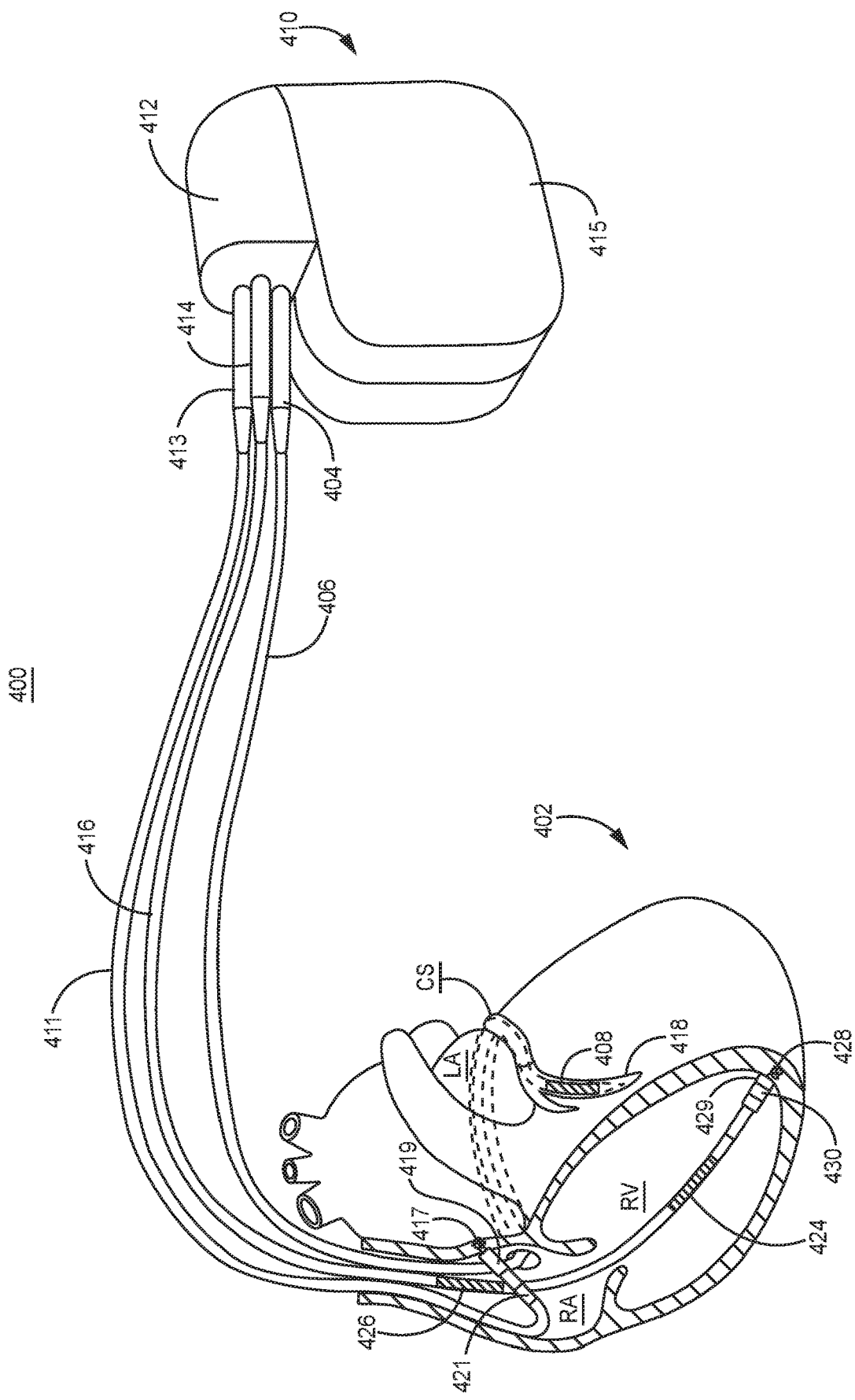
FIG. 10 is a schematic diagram of one example of a transvenous ICD system 400 in which aspects disclosed herein for controlling ATP therapy may be implemented.
Figure 11A:
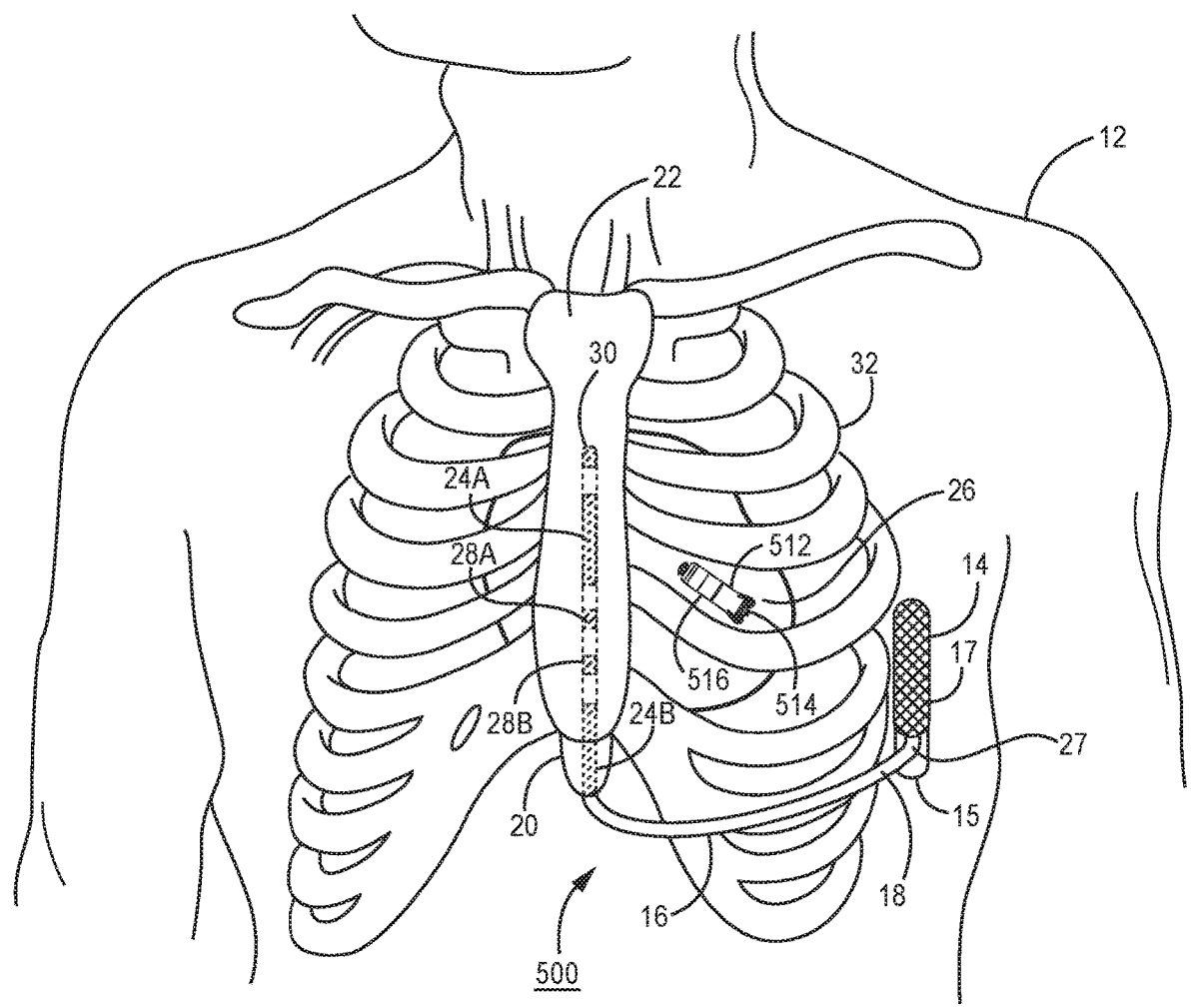
FIGS. 11A and 11B are a schematic diagrams of an implantable medical device system that includes an extra-cardiovascular ICD and an intra-cardiac pacemaker.
Figure 11B:
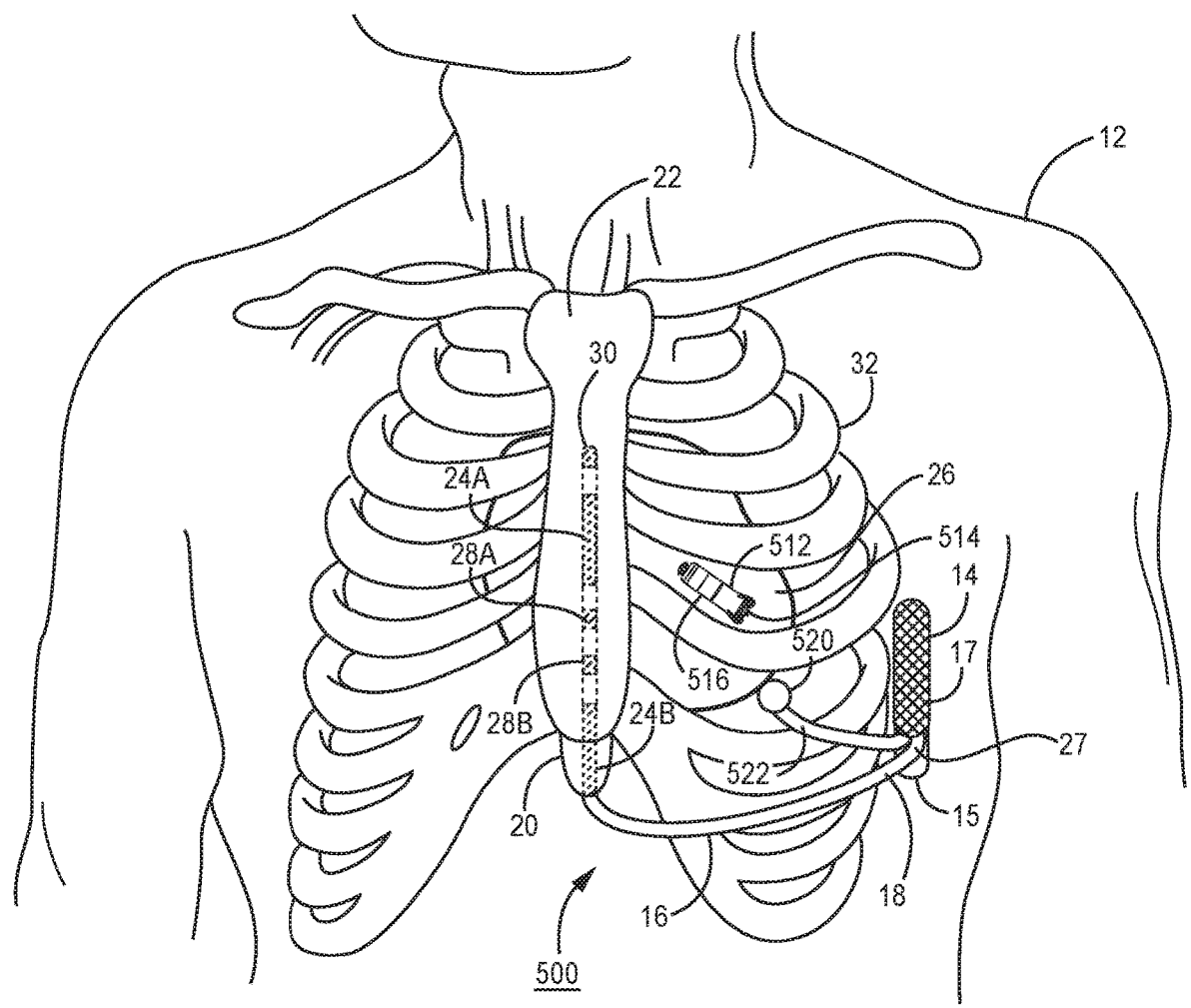

The functional blocks shown in FIG. 5 represent functionality included in ICD 14 of system 10 but are also representative of the functionality that may be included in other IMD systems, such as the systems 400 and 500 shown in the FIGS. 10 and 11 respectively, operating according to the techniques disclosed herein for controlling ATP therapy. In some IMD systems, such as the system 500 shown in FIGS. 11A and 11B which includes both an ICD 14 and an intra-cardiac pacemaker 512, the functionality represented by the modules shown in FIG. 5 may be distributed across more than one implantable medical device included in the IMD system. The functional blocks and modules shown in FIG. 5 may include any discrete and/or integrated electronic circuit components that implement analog and/or digital circuits capable of producing the functions attributed to ICD 14 herein. As used herein, the term "module" refers to an application specific integrated circuit (ASIC), an electronic circuit, a processor (shared, dedicated, or group) and memory that execute one or more software or firmware programs, a combinational logic circuit, state machine, or other suitable components that provide the described functionality. The particular form of software, hardware and/or firmware employed to implement the functionality disclosed herein will be determined primarily by the particular system architecture employed in the device and by the particular detection and therapy delivery methodologies employed by the IMD system. Providing software, hardware, and/or firmware to accomplish the described functionality in the context of any modern IMD system, given the disclosure herein, is within the abilities of one of skill in the art.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control module 80 or other ICD modules to perform various functions attributed to ICD 14 or those ICD modules. The non-transitory computer-readable media storing the instructions may include any of the media listed above.

Depiction of different features as modules is intended to highlight different functional aspects and does not necessarily imply that such modules must be realized by separate hardware or software components. Rather, functionality associated with one or more modules may be performed by separate hardware, firmware or software components, or integrated within common hardware, firmware or software components. For example, cardiac pacing operations may be performed by therapy delivery module 84 under the control of control module 80 and may include operations implemented in a processor executing instructions stored in memory 82.

Control module 80 communicates with therapy delivery module 84 and electrical sensing module 86 for sensing cardiac electrical activity, detecting cardiac rhythms, and controlling delivery of cardiac electrical stimulation therapies in response to sensed cardiac signals. Therapy delivery module 84 and electrical sensing module 86 are electrically coupled to electrodes 24A, 24B, 28A, 28B, and 30 carried by lead 16 (shown in FIGS. 1A and 1B) and the housing 15, which may function as a common or ground electrode or as an active can electrode for delivering CV/DF shock pulses.

Electrical sensing module 86 may be selectively coupled to electrodes 28A, 28B, 30 and housing 15 in order to monitor electrical activity of the patient's heart. Electrical sensing module 86 may additionally be selectively coupled to electrodes 24A and/or 24B. Sensing module 86 may include switching circuitry for selecting which of electrodes 24A, 24B, 28A, 28B, 30 and housing 15 are coupled to sense amplifiers or other cardiac event detection circuitry included in sensing module 86. Switching circuitry may include a switch array, switch matrix, multiplexer, or any other type of switching device suitable to selectively couple sense amplifiers to selected electrodes. The cardiac event detection circuitry within electrical sensing module 86 may include one or more sense amplifiers, filters, rectifiers, threshold detectors, comparators, analog-to-digital converters (ADCs), or other analog or digital components.

In some examples, electrical sensing module 86 includes multiple sensing channels for acquiring cardiac electrical signals from multiple sensing vectors selected from electrodes 24A, 24B, 28A, 28B, 30 and housing 15. Each sensing channel may be configured to amplify, filter and rectify the cardiac electrical signal received from selected electrodes coupled to the respective sensing channel to improve the signal quality for sensing cardiac events, e.g., P-waves and/or R-waves. Each sensing channel includes cardiac event detection circuitry for sensing cardiac events from the received cardiac electrical signal developed across the selected sensing electrode vector(s). For example, each sensing channel in sensing module 86 may include an input or pre-filter and amplifier for receiving a cardiac electrical signal from a respective sensing vector, an analog-to-digital converter, a post-amplifier and filter, a rectifier to produce a digitized, rectified and amplified cardiac electrical signal that is passed to a cardiac event detector included in sensing module 86 and/or to control module 80. The cardiac event detector may include a sense amplifier, comparator or other circuitry for comparing the rectified cardiac electrical signal to a cardiac event sensing threshold, such as an R-wave sensing threshold, which may be an auto-adjusting threshold. Sensing module 84 may produce a sensed cardiac event signal in response to a sensing threshold crossing. The sensed cardiac events, e.g., R-waves, are used for detecting cardiac rhythms and determining a need for therapy by control module 80. In some examples, cardiac electrical signals such as sensed R-waves are used to detect capture of a pacing pulse delivered by ICD 14.

Control module 80 is configured to analyze signals received from sensing circuit 86 for detecting tachyarrhythmia episodes. In some examples, the timing of R-wave sense event signals received from sensing circuit 86 is used control module 80 to determine RR intervals (RRIs) between consecutive R-wave sensed event signals. Control module 80 may include comparators and counters for counting RRIs that fall into various rate detection zones for determining a ventricular rate or performing other rate- or interval-based assessment for detecting and discriminating VT and VF.

For example, control module 80 may compare the RRIs to one or more tachyarrhythmia detection interval zones, such as a tachycardia detection interval zone, which may be divided into slow and fast tachycardia detection interval zones, and a fibrillation detection interval zone. RRIs falling into a detection interval zone are counted by a respective VT interval counter or VF interval counter and in some cases in a combined VT/VF interval counter included in control module 80. When an interval counter reaches a detection threshold, sometimes referred to as a "number of intervals to detect" or "NID," a ventricular tachyarrhythmia may be detected by control module 80. Control module 80 may be configured to perform other signal analysis for determining if other detection criteria are satisfied before detecting VT or VF, such as R-wave morphology criteria, onset criteria, and/or noise or oversensing rejection criteria.

In some patients, detection and therapies for both VT and VF may be enabled. In other patients, VF detection and therapies may be enabled but VT detection and therapies may be disabled. ATP therapy may be enabled for delivery following detection in either or both of these situations. The techniques disclosed herein for controlling ATP therapy may be employed following VT and/or VF detection according to programmed therapy protocols. When ATP therapy is enabled, control module 80 determines whether ATP therapy is delivered or canceled based on input received from electrical sensing module 86 and/or therapy delivery module 84 after detecting tachyarrhythmia, e.g., VT or VF.

Therapy delivery module 84 may include a low voltage (LV) therapy module 85 for delivering low voltage pacing pulses using an extra-cardiovascular pacing electrode vector selected from electrodes 24A, 24B, 28A, 28B, 30 and 15. LV therapy module 85 may be configured to deliver low voltage pacing pulses, e.g., 8 V or less or 10 V or less. One or more capacitors included in the LV therapy module 85 are charged to a voltage according to a programmed pacing pulse amplitude by a LV charging circuit, which may include a state machine. The LV charging circuit may charge the capacitors to a multiple of the voltage of a battery included in power source 98 without requiring a transformer. At an appropriate time, the LV therapy module 85 couples the capacitor(s) to a pacing electrode vector to deliver a pacing pulse to the heart 26.

HV therapy module 83 includes one or more high voltage capacitors having a higher capacitance and a higher voltage rating than the capacitor(s) included in the LV therapy module 85. When a shockable rhythm is detected, which may be a fast VT or VF, the HV capacitor(s) is(are) charged to a shock voltage amplitude by a HV charging circuit according to the programmed shock energy. The HV charging circuit may include a transformer and be a processor-controlled charging circuit that is controlled by control module 80. Control module 80 applies a signal to trigger discharge of the HV capacitor(s) upon detecting a feedback signal from therapy delivery module 84 that the HV capacitors have reached the shock voltage amplitude required to deliver the programmed shock energy. In this way, control module 80 controls operation of the high voltage therapy module 83 to deliver CV/DF shocks using defibrillation electrodes 24A, 24B and/or housing 15.

HV therapy module 83 may be used to deliver cardiac pacing pulses, including ATP pulses. In this case, the HV capacitor(s) is(are) charged to a pacing voltage amplitude that is a much lower voltage than that used for delivering shock therapies but may be higher than the maximum available pulse voltage amplitude produced by the LV therapy module 85. For example, the HV capacitor may be charged to 40 V or less, 30 V or less, or 20 V or less for producing extra-cardiovascular pacing pulses. In some cases the HV capacitor may be charged to 8 to 10 Volts for delivering ATP, but having a higher capacitance, is capable of a longer pulse width than LV therapy module 85.

Compared to pacing pulses delivered by LV therapy module 85, pulses having a higher voltage amplitude and/or relatively longer pulse width may be produced for delivering higher energy pacing pulses for capturing the heart. Longer pulse width is attainable due to a higher capacitance (and consequently higher RC time constant) of the HV capacitor(s). The LV therapy module 85 may be capable of producing a maximum pulse voltage amplitude of up to 8 V or up to and including 10 V. The maximum single-pulse pacing pulse width produced by LV therapy module 85 may be up to 2 ms or up to 4 ms in some examples. LV therapy module 85 may be configured to produce composite pacing pulses comprising two or more individual pulses fused in time to deliver a cumulative composite pacing pulse energy that captures the heart. Techniques for delivering composite pacing pulses are generally disclosed in the above-incorporated U.S. patent application Ser. No. 15/367,516 and in U.S. patent application Ser. No. 15/368,197, incorporated herein by reference in its entirety. The maximum composite pacing pulse width may be up to 8 ms or higher.

The HV therapy module 83 may be capable of producing a pulse voltage amplitude of 10 V or more and may produce mono- or multi-phasic pulses having a relatively longer pacing pulse width, e.g., 10 ms or more, because of the higher capacitance of high voltage capacitors included in HV therapy module 83. A typical HV pacing pulse width may be 10 ms; however an example range of available pulse widths may be 2 ms to 20 ms. An example of a maximum voltage amplitude that may be used for delivering high voltage pacing pulses may be 40 V. When a relatively higher pacing pulse voltage amplitude is tolerable by the patient, e.g., more than 10 V, a relatively shorter pacing pulse width, e.g., 2 to 5 ms, may be used during the pacing from HV therapy module 83. However, a longer pacing pulse width may be used as needed, e.g., a 10 V, 20 ms pacing pulse.

For the sake of comparison, the HV capacitor(s) of the HV therapy module 83 may be charged to an effective voltage greater than 100 V for delivering a cardioversion/defibrillation shock. For example, two or three HV capacitors may be provided in series having an effective capacitance of 148 to 155 microfarads in HV therapy module 83. These series capacitors may be charged to develop 750 to 800 V for the series combination in order to deliver shocks having a pulse energy of 5 Joules or more, and more typically 20 Joules or more.

In contrast, pacing pulses delivered by the HV therapy module 83 may have a pulse energy less than 1 Joule and even in the milliJoule range or tenths of milliJoules range depending on the pacing electrode impedance. For instance, a pacing pulse generated by HV therapy module 83 having a 10 V amplitude and 20 ms pulse width delivered using a pacing electrode vector between defibrillation electrodes 24A and 24B, having an impedance in the range of 20 to 200 ohms, may have a delivered energy of 5 to 7 milliJoules. When a relatively shorter pulse width is used, e.g., down to 2 ms, the pacing pulse delivered by HV therapy module 83 using defibrillation electrodes 24A and 24B (or 24A' and 24B') may be as low as 1 milliJoule. Pacing pulses delivered by HV therapy module 83 are expected to have a pacing voltage amplitude that is less than 100 V, and typically not more than 40 V, and deliver at least 1 milliJoule but less than 1 Joule of energy. The delivered energy for a given pacing voltage amplitude will vary depending on the pulse width and pacing electrode vector impedance.

If a pace/sense electrode 28A, 28B or 30 is included in the pacing electrode vector, resulting in a relatively higher impedance, e.g., in the 400 to 1000 ohm range, the pacing pulse energy delivered may be in the range of 2 to 5 milliJoules. In contrast, pacing pulses delivered by a LV therapy module included in a transvenous ICD system or intra-cardiac pacemaker, e.g., as shown in FIGS. 10 and 11, respectively, using endocardial electrodes may be on the order of microJoules, e.g., 2 microJoules to 5 microJoules for a typical endocardial pacing pulse that is 2V in amplitude, 0.5 ms in pulse width and applied across a pacing electrode vector impedance of 400 to 1000 ohms.

HV therapy module 83 may deliver more current via a lower impedance pacing electrode vector, e.g., between defibrillation electrodes 24A and 24B or 24A' and 24B', than the current delivered by LV therapy module 85 via a pacing electrode vector including a pace/sense electrode 28A, 28B or 30 (relatively higher impedance) even when the pacing voltage amplitude is the same.

In some instances, control module 80 may control impedance measurement module 90 to determine the impedance of a pacing electrode vector. Impedance measurement module 90 may be electrically coupled to the available electrodes 24A, 24B, 28A, 28B, 30 and housing 15 for performing impedance measurements of one or more candidate pacing electrode vectors. Control module 80 may control impedance measurement module 90 to perform impedance measurements by passing a signal to impedance measurement module 90 to initiate an impedance measurement of a pacing electrode vector. Impedance measurement module 90 is configured to apply a drive or excitation current across a pacing electrode vector and determine the resulting voltage. The voltage signal may be used directly as the impedance measurement or impedance may be determined from the applied current and the measured voltage. The impedance measurement may be passed to control module 80.

Figure 6:
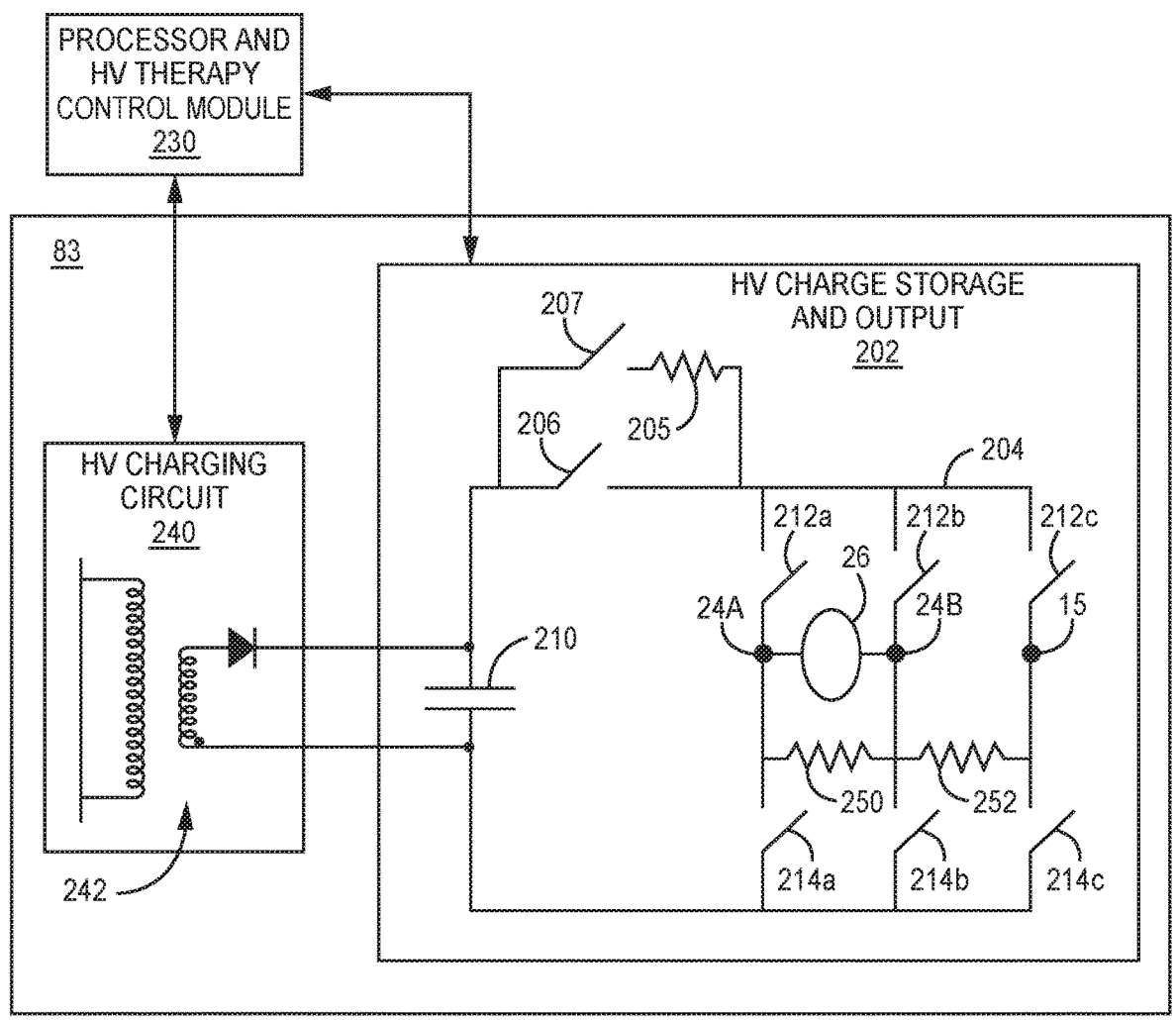
FIG. 6 is schematic diagram of HV therapy module coupled to a processor and HV therapy control module.

As described in conjunction with FIG. 6, control module 80 may use the impedance measurement to set a variable shunt resistance included in HV therapy module 83 when HV therapy module 83 is delivering pacing pulses to heart 26. The variable shunt resistance may be parallel to the pacing load and set to maintain electrical current through HV therapy module switching circuitry throughout the duration of a pacing pulse delivered by the HV therapy module 83 thereby promoting an appropriate voltage signal across the pacing load for capturing the patient's heart.

Control parameters utilized by control module 80 for detecting cardiac rhythms and delivering electrical stimulation therapies and tachyarrhythmia induction pulses may be programmed into memory 82 via telemetry module 88. Telemetry module 88 includes a transceiver and antenna for communicating with external device 40 (shown in FIG. 1A) using RF communication as described above. Under the control of control module 80, telemetry module 88 may receive downlink telemetry from and send uplink telemetry to external device 40. In some cases, telemetry module 88 may be used to transmit and receive communication signals to/from another medical device implanted in patient 12.

FIG. 6 is schematic diagram 200 of HV therapy module 83 coupled to a processor and HV therapy control module 230. HV therapy module 83 includes a HV charging circuit 240 and a HV charge storage and output module 202. Processor and HV therapy control module 230 may be included in control module 80 for controlling HV charging circuit 240 and HV charge storage and output module 202. HV charge storage and output module 202 includes a HV capacitor 210 coupled to switching circuitry 204 via a pulse control switch 206 for coupling the HV capacitor 210 to electrodes 24a, 24b and/or housing 15 to deliver a desired electrical stimulation pulse to the patient's heart 26. HV capacitor 210 is shown as a single capacitor, but it is recognized that a bank of two or more capacitors or other energy storage devices may be used to store energy for producing electrical signals delivered to heart 26. In one example, HV capacitor 210 is a series of three capacitors having an effective capacitance of 148 to 155 microfarads with a high voltage rating to enable charging up to an effective charge of 800 V or more. In contrast, holding capacitors that are included in LV therapy module 85 that are charged to a multiple of the battery voltage by a state machine or capacitor charge pump circuit may have a capacitance of up to 6 microfarads, up to 10 microfarads, up to 20 microfarads or other selected capacitance, but all have a capacitance significantly less than the effective capacitance of high voltage capacitor 210. The LV therapy module 85 has a lower breakdown voltage than the HV therapy module 83, allowing the HV capacitor 210 to be charged to the shock voltage amplitude required for delivering CV/DF shocks.

HV charging circuit 240 receives power from power source 98 (FIG. 5) for charging capacitor 210 as needed. HV charging circuit 240 includes a transformer 242 to step up the battery voltage of power source 98 in order to achieve charging of capacitor 210 to a voltage that is much greater than the battery voltage. Charging of capacitor 210 by HV charging circuit 240 is performed under the control of processor and HV therapy control 230, which receives feedback signals from HV charge storage and output module 202 to determine when capacitor 210 is charged to a programmed voltage. A charge completion signal is passed to HV charging circuit 240 to terminate charging by processor and HV therapy control module 230. One example of a high voltage charging circuit and its operation is generally disclosed in U.S. Pat. No. 8,195,291 (Norton, et al.), incorporated herein by reference in its entirety.

When control module 80 determines that delivery of an electrical stimulation pulse from HV therapy module 83 is needed, switching circuitry 204 is controlled by signals from processor and HV therapy control module 230 to electrically couple HV capacitor 210 to a therapy delivery vector to discharge capacitor 210 across the vector selected from electrodes 24a, 24b and/or housing 15. Switching circuitry 204 may be in the form of an H-bridge including switches 212a-212c and 214a-214c that are controlled by signals from processor and HV control module 230. Switches 212a-212c and 214a-214c may be implemented as silicon-controlled rectifiers (SCRs), insulated-gate bipolar transistors (IGBTs), metal-oxide-semiconductor field-effect transistors (MOSFETs), and/or other switching circuit components. The selected electrodes 24a, 24b and/or housing 15 are coupled to HV capacitor 210 by opening (i.e., turning off or disabling) and closing (i.e., turning on or enabling) the appropriate switches of switching circuitry 204 to pass a desired electrical signal to the therapy delivery electrode vector, which may be a shock electrode vector or a pacing electrode vector that is the same or different that the shock electrode vector. While only electrodes 24A, 24B and housing 14 are indicated in as being coupled to switching circuitry 204, it is to be understood that pace/sense electrodes 28A, 28B and 30 may be coupled to switching circuitry 204 and available for use in a pacing electrode vector.

When control module 80 determines that a shock therapy is needed based on a detected heart rhythm, e.g., VT or VF, the electrical signal delivered by HV therapy module 83 may be a monophasic, biphasic or other shaped CV/DF shock pulse for terminating the ventricular tachyarrhythmia. When control module 80 determines that a pacing therapy is needed based on a VT or VF detection, HV therapy module 83 may deliver a series of monophasic or biphasic pacing pulses according to a programmed ATP protocol. Methods for confirming ATP delivery criteria and controlling the timing of ATP therapy delivery are described below, e.g., in conjunction with the accompanying flow charts of FIGS. 7 and 8 and 12.

In some examples, when a biphasic CV/DF shock or biphasic pacing pulse is needed, one of switches 212a, 212b and 212c may be closed simultaneously with one of switches 214a, 214b and 214c without closing both of the "a," "b" or "c" switches across a given electrode 24a, 24b or housing 15, respectively, at the same time. To deliver a biphasic pulse using electrode 24a and housing 15, for instance, switch 212a and 214c may be closed to deliver a first phase of the biphasic pulse. Switches 212a and 214c are opened after the first phase, and switches 212c and 214a are closed to deliver the second phase of the biphasic pulse. Switches 212b and 214b remain open or disabled in this example with electrode 24b not selected or used in the therapy delivery vector. In other examples, electrode 24B may be included instead of electrode 24A or simultaneously activated with electrode 24A by closing switch 212b during the first phase and closing switch 214b in the second phase of the illustrative biphasic pulse. The first phase of a biphasic pulse may be terminated when the pulse voltage amplitude has decayed according to a programmed "tilt" or percentage of the leading voltage amplitude of the pacing pulses. For example, the first phase may be terminated when the pulse voltage amplitude has decayed to 50% of the leading voltage amplitude.

In response to detecting a tachyarrhythmia for which ATP pacing therapy is enabled, control module 80 prepares HV therapy module 83 to deliver ATP by adjusting the electrical charge of capacitor 210 to a programmed pacing voltage amplitude under the control of processor and HV therapy control module 230. In some instances, HV capacitor 210 may be charged up to the pacing voltage amplitude by HV charging circuit 240. At other times, HV capacitor 210 may retain a residual charge after being charged for a previous therapy, e.g., a previous pacing therapy or CV/DF shock delivery, or for capacitor maintenance. In this case, HV capacitor 210 may be adjusted to the pacing voltage amplitude by electrically coupling HV capacitor 210 to a non-therapeutic load 205 shown schematically in FIG. 6, for dumping energy to reduce the charge of HV capacitor 210 from the residual charge to the pacing voltage amplitude. The non-therapeutic load 205 may be a resistor or bank of resistors in therapy delivery module 84 and in some examples may utilize shunt resistors 250 and 252. A charge dumping switch 207 may be closed by processor and HV therapy control 230 to discharge HV capacitors 210 through the non-therapeutic load 205.

After confirming that the HV capacitor 210 has reached the pacing voltage amplitude, and after any ATP delivery criteria confirmation required for ATP therapy delivery as described in conjunction with the techniques described below, including FIG. 7, ATP pulses are delivered. Switches 212a-212c and 214a-214c are controlled to be open or closed by processor and HV therapy control module 230 at the appropriate times for delivering a monophasic, biphasic or other desired ATP pulse by discharging capacitor 210 across the pacing load presented by heart 26 and a selected pacing electrode vector. The capacitor 210 is coupled across the selected pacing electrode vector for the programmed pacing pulse width by controlling pulse control switch 206.

HV charge storage and output module 202 is shown to include an optional shunt resistance 250 in parallel to the pacing load shown schematically as heart 26 when electrodes 24A and 24B are selected as the anode and cathode (or cathode and anode, respectively) of the pacing electrode vector. It is recognized that a shunt resistance may be provided in parallel to the pacing load for any selected pacing electrode vector, for example shunt resistance 252 is shown schematically if the pacing electrode vector includes electrode 24B and housing 15. Likewise a shunt resistance may be provided in parallel to the pacing load when the pacing electrode vector includes electrode 24A and housing 15.

Switches 212a-212c and switches 214a-214c may require a minimum current flow to hold them closed (i.e., ON or enabled) for passing current as capacitor 210 is discharged. This minimum current may be on the order of approximately 10 milliamps. Depending on the pacing load impedance and other conditions, the electrical current passing through enabled switches of switches 212a-212c and 214a-214c may fall below the minimum current required to keep the switches closed as capacitor 210 is discharged across a selected pacing vector. If the current passing through a respective switch falls below the minimum current required to keep the switch closed, the switch may open (or become disabled) causing premature truncation of the pacing pulse, which could result in loss of capture. As such, a minimum pacing pulse voltage amplitude may be set for delivering pacing pulses from HV therapy module 83 in order to reduce the likelihood of the electrical current produced during capacitor 210 discharge falling below the minimum current required to maintain a stable state of enabled switches of switching circuitry 204 during a programmed pacing pulse width.

The shunt resistance 250 or 252 may be a variable resistance that is set to match a pacing electrode vector impedance so that the load across heart 26 using a selected pacing electrode vector matches the shunt resistance. In this way, current through the switching circuitry 204 may be maintained at or above a minimum current required to maintain a stable state of enabled switches of switching circuitry 204 during the pacing pulse. The shunt resistance 250 may be set to a resistance that maintains the electrical current to selected switches of switching circuitry 204 at or above the minimum current required to hold the selected switches in the closed or enabled state.

If the shunt resistance 250 or 252 is lower than the pacing electrode vector impedance, current produced by discharging capacitor 210 may be shunted away from the pacing load, e.g., the pacing electrode vector between electrodes 24a and 24b and heart 26, potentially resulting in less energy delivered to heart 26, which may result in loss of capture. Accordingly, processor and HV therapy control module 230 may be configured to retrieve a pacing electrode vector impedance measurement from impedance measurement module 90 and set the shunt resistance 250 (or 252) to match the pacing electrode vector impedance.

In other examples, a minimum voltage charge of capacitor 210 may be set to provide the minimum current required to maintain an enabled state of selected switches of switching circuitry 204, but pacing energy may be intentionally shunted away from the pacing load including heart 26 in order to reduce the delivered pacing pulse energy. If the pacing amplitude capture threshold is below the minimum voltage amplitude required to maintain the minimum current to keep switches 212a-212c and 214a-214c on when they are enabled by processor and HV therapy control module 230, the energy delivered across the pacing electrode vector may be reduced by setting the variable shunt resistance 250 (or 252) to a value that is less than the pacing electrode vector impedance. This current shunting may reduce skeletal muscle recruitment caused by the extra-cardiovascular pacing pulse while still providing effective capture of heart 26.

Since the range of pacing load impedances and pacing voltage amplitudes may vary between patients and over time within a patient, a variable shunt resistance may be provided to enable selection of the appropriate resistance for shunting the required current through the switching circuitry 204. It is contemplated, however, that in some examples a fixed resistance shunt may be provided. For example, the resistance needed to shunt current to the switching circuitry 204 when the pacing load impedance is high may still shunt some current to the switching circuitry when the pacing load impedance is relatively lower. An optimal value for a fixed resistance shunt may be determined based on empirical data, e.g., typical pacing load impedances and pacing pulse voltage amplitudes used clinically.

The pacing electrode vector coupled to HV capacitor 210 via switching circuitry 204 may include electrodes 24a, 24b, 28a, 28b and/or 30 carried by lead 16. Housing 15 may be unused for cardiac pacing pulse delivery by holding switches 212c and 214c open. Depending on the implant location of ICD 14 and lead 16 and the resulting electrical stimulation delivery vector between the housing 15 and an electrode 24a, 24b, 28a, 28b or 30, greater recruitment of skeletal muscle may occur when housing 15 is included in the pacing electrode vector. A larger volume of skeletal muscle tissue may lie along a vector extending between the distal portion 25 of lead 16 and housing 15 than along a vector extending between the two electrodes carried by lead distal portion 25. In the example configurations of FIGS. 1A-2C, for example, a pacing pulse may be delivered between electrodes 24a and 24b, between electrodes 28A and 28B, between electrodes 28A and 24A or between electrodes 28B and 24B to limit skeletal muscle recruitment compared to a pacing electrode vector that includes housing 15. In other electrode configurations and implant locations, the electrodes used to deliver extra-cardiovascular pacing pulses by HV therapy module 83 may include housing 15 and may be selected to provide a pacing electrode vector that minimizes the volume of skeletal muscle recruited during pacing pulse delivery while still directing sufficient energy to the heart 26 for capturing and pacing the heart.

Figure 7:
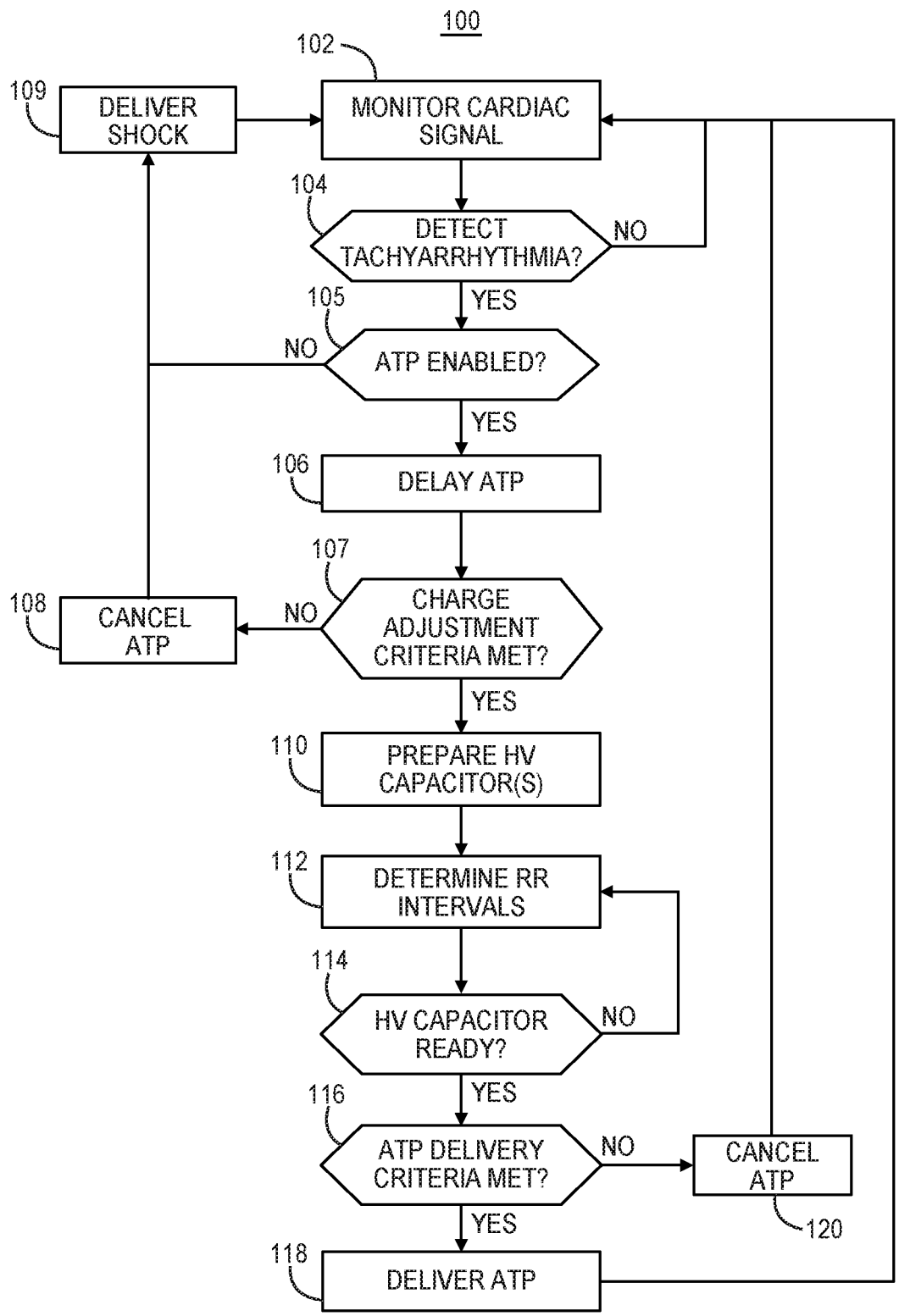
FIG. 7 is a flow chart of a method for controlling ATP delivery according to one example.

FIG. 7 is a flow chart 100 of a method for controlling ATP therapy delivery by HV therapy module 83 according to one example. At block 102, control module 80 monitors the cardiac electrical signal(s) received from sensing circuit 86 for detecting tachyarrhythmia. As described above, control module 80 may at least determine RRIs between consecutive R-wave sensed event signals received from sensing circuit 86 for detecting ventricular tachyarrhythmias. Control module 80 may include tachyarrhythmia interval counters for counting RRIs as they are determined that fall into a VT interval zone and/or a VF interval zone. If VT detection is enabled and a VT internal counter reaches a threshold number of intervals to detect (NID) set for detecting VT, VT may be detected at block 104. If a VF interval counter reaches an NID set for detecting VF, VF may be detected at block 104. In other examples, control module 80 may be configured to perform additional signal analyses of sensed waveforms and/or longer segments of the cardiac electrical signal(s), such as morphological analysis for confirming R-waves or discriminating supraventricular tachyarrhythmia, analysis for electrical noise detection, T-wave oversensing detection, and/or other signal analysis. Additional signal analysis may be performed on one or more sensing electrode vector signals in various combinations. Examples of tachyarrhythmia detection methods are generally disclosed in U.S. Pat. No. 6,393,316 (Gillberg et al.); U.S. Pat. No. 7,031,771 (Brown, et al.); U.S. Pat. No. 8,160,684 (Ghanem, et al.), U.S. Pat. No. 8,437,842 (Zhang, et al.) and provisional U.S. Pat. Application No. 62/367,166 (filed Jul. 27, 2016), all of which are incorporated herein by reference in their entirety.

If tachyarrhythmia is detected at block 104, the control module 80 determines if ATP therapy is enabled at block 105 according to a programmed therapy protocol. If the programmed therapy protocol includes ATP delivery prior to attempting a CV/DF shock, as determined at block 105, control module 80 may advance to block 110 to prepare the HV capacitor of HV therapy module 83 for ATP delivery. If ATP is not enabled for delivery following tachyarrhythmia detection, control module 80 may control HV therapy module 83 to charge the HV capacitor 210 to a shock voltage amplitude according to a programmed shock energy and deliver a CV/DF shock at block 109. Control module 80 returns to block 102 after therapy delivery to monitor the cardiac signal for redetecting the tachyarrhythmia episode if not successfully terminated or, if terminated, detecting a new episode in the future.

If ATP is enabled at block 105, control module 80 delays the ATP therapy at block 106 for a period of time during which control module 80 may determine if ATP delivery criteria are met and/or may prepare the HV capacitor 210 for ATP delivery. Control module 80 may optionally determine whether charge adjustment criteria are met at block 107 based on the charge of HV capacitor 210. For example, if the charge of HV capacitor 210 is greater than a charge adjustment threshold at block 107, charge adjustment criteria may be determined to be unmet.

In some instances, HV capacitor 210 may retain a residual charge from a preceding therapy or capacitor maintenance charging that is greater than the programmed pacing voltage amplitude to be used for delivering ATP. In some cases, residual charge may be dumped after a high voltage therapy or capacitor maintenance charging to enable the HV capacitor 210 to be ready for charging to the pacing voltage amplitude. However, a residual charge may remain on the HV capacitor 210 at the time that the tachyarrhythmia is detected and ATP is needed. The process of adjusting the HV capacitor charge from a relatively high voltage to the pacing voltage amplitude for ATP by charge dumping through a non-therapeutic load may result in an unacceptable delay time between tachyarrhythmia detection and therapy delivery. In some examples, therefore, if the HV capacitor charge is greater than a charge adjustment threshold, control circuit 80 may cancel the ATP therapy at block 108 and advance to block 109 to deliver the next therapy in a menu of therapies programmed for treating the detected tachyarrhythmia, e.g., a shock therapy.

The charge adjustment threshold used to determine if charge adjustment criteria are met for timely delivery of ATP from the HV therapy module 83 may be a predetermined voltage that is greater than the pacing voltage amplitude and less than the shock voltage amplitude corresponding to a programmed shock energy. For example, the HV capacitor charge may be compared to the pacing voltage amplitude plus a predetermined charge difference. The predetermined charge difference may be on the order of 20 to 40 Volts in some examples. In other examples, the charge adjustment threshold may be a predetermined percentage of the shock voltage amplitude or a predetermined percentage of the pacing voltage amplitude, for example twice the pacing voltage amplitude.

In still other examples, the difference between the HV capacitor charge at the time of tachyarrhythmia detection and the programmed pacing voltage amplitude may be determined at block 107, and this difference may be compared to a charge adjustment threshold. If the difference is not greater than the charge adjustment threshold, control module 80 may advance to block 110 to prepare the HV capacitor 210 for ATP delivery. The charge adjustment threshold may be defined based on the time duration necessary to dump the voltage difference through a non-therapeutic load. If the difference is greater than the charge adjustment threshold, the time required to dump excess charge may unacceptably delay therapy for terminating the detected tachyarrhythmia. In that case, control module 80 may advance to block 108 and cancel the ATP therapy.

To illustrate, if the HV capacitor 210 is charged to 520 V and the programmed ATP pacing voltage amplitude is 20 V, the charge difference is 500 V. The time to dump the excess 500 V charge may be approximately fifteen seconds, depending on the RC time constant of the non-therapeutic load, which may be an unacceptably long delay in therapy delivery. In this case, control module 80 would make the decision to cancel ATP and deliver a shock therapy at blocks 108 and 109, respectively. However, if the HV capacitor charge is 50 V at the time of detecting the tachyarrhythmia and the ATP pacing voltage amplitude is 20 V, the time required to dump the excess 30 V through a non-therapeutic load may be approximately two seconds. In this case, control module 80 may advance to block 110 to begin preparing the HV capacitor 210 for ATP delivery. The charge adjustment threshold may be set based on a charge difference that can be dumped through the non-therapeutic load 205 within a predetermined acceptable ATP delay time. Acceptable ATP delay time may be 10 seconds, 8 seconds, 5 seconds, 3 seconds, 2 seconds, or another predetermined time interval.

In another example, control module 80 may determine an estimated time to dump the excess charge based on the charge difference between the HV capacitor charge and the ATP pacing voltage amplitude and a known RC time constant of HV capacitor 210 and the non-therapeutic load. Estimated charge dumping time may be computed or fetched from a look-up table stored in memory 82 for a range of different charge difference values. The charge adjustment criteria may be determined to be met at block 107 when the estimated charge dumping time is less than or equal to a predetermined acceptable therapy delay time.

In some examples, the ATP pulses may be delivered at a pulse voltage amplitude that is at or within a tolerance range of the programmed pacing voltage amplitude for ATP. For example, a voltage tolerance may be set to a fixed voltage interval or a percentage of the programmed ATP pacing voltage amplitude. Determination of whether the charge adjustment criteria are met at block 107 may be based on the programmed pacing voltage amplitude plus the tolerance. For instance, the tolerance may be set to a fixed value, e.g., 5 Volts, or a percentage of the programmed pacing voltage amplitude, e.g., 20%. In some examples, the tolerance may be zero. If the charge difference between the HV capacitor charge at the time of the tachyarrhythmia detection and the pacing voltage amplitude plus the tolerance is less than a charge adjustment threshold, or the time to dump charge down to the pacing voltage amplitude plus the tolerance is less than or equal to an acceptable therapy delay time, the charge adjustment criteria may be determined to be met at block 107.

At block 110, control module 80 controls HV therapy module 83 to prepare the HV capacitor 210 for delivery of ATP by adjusting the charge of the HV capacitor 210 to the programmed pacing voltage amplitude or within a predetermined tolerance thereof. The HV capacitor 210 may need to be charged to the programmed pacing voltage amplitude for delivering ATP pulses when the HV capacitor charge at the time of the tachyarrhythmia detection is less than the pacing voltage amplitude. At other times a residual charge may remain after a previous CV/DF shock or other previous therapy or after capacitor maintenance charging. If the residual charge of the HV capacitor 210 is greater than the programmed pacing voltage amplitude for ATP delivery, but charge adjustment criteria are met at block 107, the HV therapy module 83 is adjusted to the pacing voltage amplitude by controlling the HV charge storage and output module 202 to dump energy at block 110 by discharging the HV capacitor 210 through a non-therapeutic load 205 (FIG. 6).

The processor and HV therapy control module 230 may monitor the voltage of HV capacitor 210 and terminate the energy dumping when the capacitor voltage reaches the pacing voltage amplitude. In some instances, the capacitor voltage may fall below the pacing voltage amplitude during energy dumping and the HV charging circuit 240 may be controlled to recharge the HV capacitor 210 to the pacing voltage amplitude. In other instances, control module 230 may determine that the HV capacitor is prepared and ready for ATP therapy delivery once the HV capacitor charge reaches the programmed pacing voltage amplitude plus a tolerance. If the time required for charge dumping to the programmed pacing voltage amplitude exceeds an acceptable ATP therapy delay time, the charge dumping may be terminated when the HV capacitor charge reaches the pacing voltage amplitude plus a tolerance, e.g., 5 V or other fixed value or a predetermined percentage of the pacing voltage amplitude, e.g., 20%.

While control module 80 waits for an ATP therapy delay period while the HV capacitor preparation is occurring at block 110, control module 80 may determine one or more RRIs at block 112, after the VT or VF detection has been made. In response to a signal from processor and HV therapy control module 230 indicating that the HV capacitor charge is at the pacing voltage amplitude (or within a voltage tolerance of the pacing voltage amplitude) and ready for ATP delivery (block 114), control module 80 determines if ATP delivery criteria are met at block 116. One or more of the RRIs determined during HV capacitor preparation may be compared to a synchronization interval at block 116. At least the earliest RRI immediately following confirmation of the HV capacitor charge being at the pacing voltage amplitude or the most recent RRI immediately preceding confirmation of the HV capacitor charge being at the pacing voltage amplitude is compared to the synchronization interval. If a threshold number of RRIs are greater than the synchronization interval, the ATP delivery criteria may be unmet at block 116.

The synchronization interval may be established by control module 80 at block 116 based on the rate of the detected tachyarrhythmia. For example, a mean or median RRI may be determined from a predetermined number of RRIs immediately prior to VT or VF detection (or redetection). In one example, six most recent RRIs prior to detection are used for determining the synchronization interval. The minimum and the maximum of the six RRIs may be dropped and the mean RRI of the remaining four RRIs is determined. A fixed interval, e.g., 60 ms, may be added to the mean to determine the synchronization interval.

In other examples, the synchronization interval may be established by control module 80 at block 116 based on the longest programmed tachyarrhythmia detection interval. When VT detection is enabled, the synchronization interval may be the VT detection interval or the VT detection interval plus a fixed interval. For example, if the maximum VT detection interval is 360 ms, the synchronization interval may be the VT detection interval plus a fixed interval, e.g., 0 to 60 ms. If VT detection is not enabled, the synchronization interval may be the longest VF detection interval, e.g., 320 ms plus a fixed interval, e.g., 0 to 60 ms.

In some examples, the synchronization interval is determined at block 116 based on the detected rate, e.g., using the most recent six (or other predetermined number of RRIs), unless the last RRIs prior to detection have a range greater than a range threshold. For example, if the largest and smallest RRIs out of the last six RRIs prior to detection are within 50 ms of each other, the synchronization interval is determined based on the mean of the remaining four RRIs, referred to as the "trimmed mean." If the largest and smallest RRIs out of the six RRIs are more than 50 ms apart, the synchronization interval is determined based on the longest detection interval for the rhythm being detected plus a fixed interval. In still other examples, the synchronization interval may be determined by control module 80 as being the largest one out of the maximum detection interval and trimmed mean. For instance if the tachyarrhythmia is detected based on RRIs in the VF interval zone, the synchronization interval may be set as the maximum fibrillation detection interval or the trimmed mean, whichever is greater, plus 60 ms.

If a threshold number of RRIs determined during the HV capacitor preparation are less than the synchronization interval at block 116, the ATP delivery criteria are met. In one example, if at least X out of Y RRIs determined after tachyarrhythmia detection and during (and/or after) the HV capacitor preparation are less than or equal to the synchronization interval, the ATP delivery criteria are met. The values of X and Y may be programmable where X may be one or more and Y is any value equal to or greater than X. For example, 3 out of 4 RRIs may be required to be less than the synchronization interval though other ratios or percentages may be used.

In some cases Y RRIs may not be reached during the HV capacitor preparation. If fewer than Y RRIs have occurred when the HV capacitor is ready for ATP delivery at block 114, control module 80 may determine the most recent RRI and compare it to the synchronization interval. If the most recent RRI is less than the synchronization interval, the ATP delivery criteria are met at block 116. In other examples, the ATP delivery criteria requires that two or more most recent RRIs, either immediately preceding and/or immediately following the completion of HV capacitor preparation, be less than the synchronization interval.

In other examples, the ATP delivery criteria may require that at least the most recent RRI is greater than a minimum ATP pacing interval or minimum synchronization interval for delivering ATP. If the most recent RRI, or a threshold number of the determined RRIs are shorter than the minimum synchronization interval, the ATP delivery criteria may be unmet at block 116. In some instances, for example if asystole occurs, control module 80 may be unable to determine an adequate number of RRIs for determining if ATP delivery criteria are satisfied. In this case, the ATP delivery criteria may be determined to be unmet at block 116.

In response to the ATP delivery criteria being met, ATP is delivered at block 118. The HV therapy module 83 is controlled to deliver the first ATP pulse synchronized to the latest sensed R-wave that occurred at an RRI confirmed to be less than (or equal to) the synchronization interval. The first ATP pulse is synchronized to a sensed R-wave by setting the first ATP pacing interval to an interval less than the detected rate of the tachyarrhythmia (and less than the synchronization interval) and delivering the first ATP pulse upon expiration of the pacing interval. The first and subsequent ATP pulses are delivered by discharging the HV capacitor 210 via the switching circuitry 204 according to a programmed ATP protocol, e.g., a burst of 6 to 10 pulses delivered at a rate that is faster than the detected tachyarrhythmia rate and according to a programmed pacing voltage amplitude and pacing pulse width.

At least the first, leading pulse of the ATP pulses is delivered having the pacing voltage amplitude. The HV capacitor 210 may be recharged to the pacing voltage amplitude prior to each ATP pulse, after delivering the preceding ATP pulse, to deliver all the ATP pulses having the pacing voltage amplitude. In other examples, the first pulse may be delivered at the pacing voltage amplitude and subsequent pulses may be delivered at a different voltage amplitude. Subsequent pulses may be delivered at a lower voltage amplitude, for example, and may have the same or a longer pulse width than the leading ATP pulse. The leading ATP pulse may be delivered with a relatively higher pacing voltage amplitude to ensure capture and paced control of the heart rhythm. After ATP delivery, control module 80 returns to block 102 to continue monitoring the cardiac signal for detecting or redetecting tachyarrhythmia.

If the ATP delivery criteria are not met at block 116, the delayed ATP therapy is withheld at block 120. The control module 80 may return to block 102 to continue monitoring the cardiac signal. The detected tachyarrhythmia may have slowed or spontaneously terminated such that ATP is no longer required. The HV capacitor 210 may be held at the pacing voltage amplitude reached during HV capacitor preparation performed at block 110 when ATP therapy is withheld such that if the tachyarrhythmia is redetected or a subsequent tachyarrhythmia is detected before other therapy is needed, the HV therapy module 83 is ready to deliver ATP if the ATP delivery criteria do become satisfied.

In other cases, after canceling ATP at block 120, a fast VT or VF may be detected as a shockable rhythm at block 105 that requires shock therapy. In this case, control module 80 may advance to block 109 without delivering ATP and may charge the HV capacitor 210 from the pacing voltage amplitude held after canceling ATP to a shock voltage amplitude corresponding to a programmed shock energy. A CV/DF shock pulse is then delivered at block 109.

Figure 8:
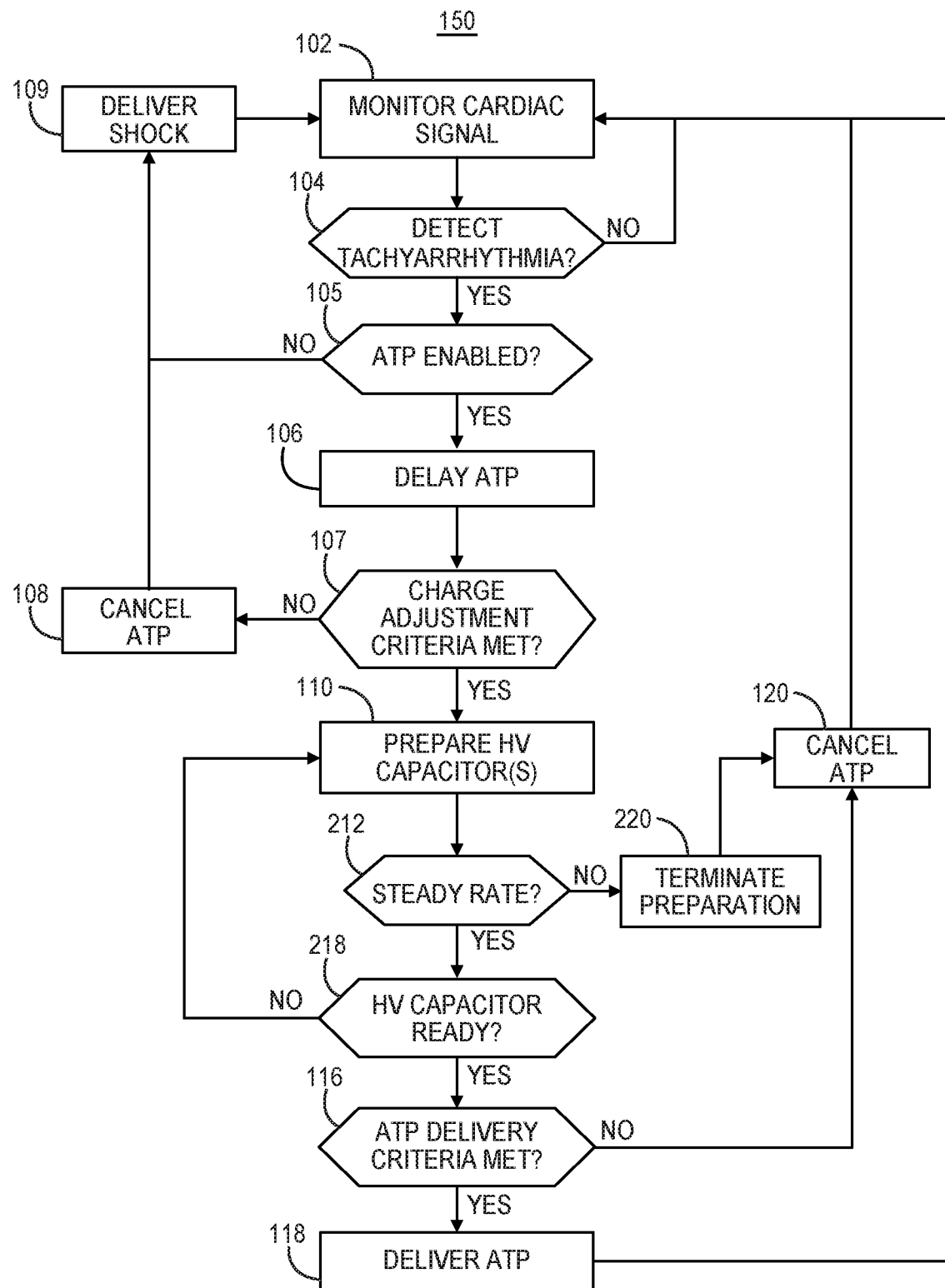
FIG. 8 is a flow chart of a method for controlling ATP delivery according to another example.

FIG. 8 is a flow chart 150 of a method for controlling ATP delivery by ICD 14 according to another example. Operations performed at blocks 102-110, 116, 118, and 120 in flow chart 150 may generally correspond to identically-numbered blocks shown in FIG. 7 and described above. In FIG. 8, RRIs are determined at block 212 by control module 80 to determine if the rate of the detected tachyarrhythmia has changed or is steady since the detection was made at block 104. Control module 80 may determine if the rate is steady, slowing, or accelerating at block 212. This determination may be made by determining the synchronization interval (as described above) and comparing RRIs determined during the HV capacitor preparation to the synchronization interval and/or other threshold intervals based on the synchronization interval. The heart rate may be determined to be steady if a predetermined percentage of the RRIs determined during the HV capacitor adjustment are within an interval range corresponding to the detected tachyarrhythmia rate or within an interval range based on the synchronization interval. The interval range may extend from an accelerating threshold interval to a slowing threshold interval.

If a predetermined percentage of the determined RRIs, or X out Y determined RRIs, are longer than a slowing threshold interval the tachyarrhythmia rate may be determined to be slowing at block 212. A slowing threshold interval may be determined by control module 80 as the synchronization interval plus a time interval, e.g., the synchronization interval plus 30 to 80 ms. It is contemplated that other methods may be used to detect a slowing rate of the detected tachyarrhythmia, e.g., by comparing consecutive RRIs to each other, to a running average or other techniques for detecting an increasing trend of the RRIs after tachyarrhythmia detection compared to before tachyarrhythmia detection.

If a predetermined percentage of RRIs or X out Y RRIs are shorter than an accelerating threshold interval, the tachyarrhythmia rate may be determined to be an accelerating rate. The accelerating threshold interval may be set as the synchronization interval less a time interval, e.g., 30 to 80 ms less than the synchronization interval. In this illustrative example, the tachyarrhythmia rate is determined as being steady if the predetermined percentage or X out of Y RRIs fall within the range between the slowing threshold interval and the accelerating threshold interval, which may be referred to as a steady rate interval range.

If the rate is determined to be steady at block 212, control module 80 may determine if the HV capacitor is ready at block 218. If the HV capacitor is not yet at the pacing voltage amplitude, control module 80 may return to block 110 to continue adjusting the HV capacitor charge and continue comparing RRIs to the rate criteria at block 212.

If the rate is steady and the HV capacitor is ready, "yes" branch of block 218, control module 80 may proceed to verifying whether the ATP delivery criteria are met at block 116 as described above in conjunction with FIG. 7. In some examples, the ATP delivery criteria may be determined as being met based on determining a steady rate. The ATP therapy may be delivered at block 118, with the first ATP pulse synchronized to the earliest sensed R-wave occurring at an RRI less than or equal to the synchronization interval after the HV capacitor is ready.

If the rate is non-steady ("no" branch of block 212), e.g., if the rate is slowing or accelerating based on sensed event intervals not remaining within an interval range, HV capacitor preparation may be terminated at block 220 in some examples. For example, if charge is being dumped for adjusting the HV capacitor 210 to the pacing voltage amplitude, the charge dumping may be terminated. If the HV capacitor 210 is being charged to the pacing voltage amplitude, the charging may be terminated. If the rate is slowing, the arrhythmia may be spontaneously terminating, and no therapy may be needed.

If the rate is accelerating, however, a therapy may still be required. In the case of an accelerating rate, capacitor charging to at least the pacing voltage amplitude may be completed at block 220 even though ATP is canceled at block 120. The HV capacitor charge may be held at the pacing voltage amplitude in anticipation of a needed therapy. If charge dumping is being performed at the time of determining that the rate is accelerating, charge dumping may be terminated at block 220 and the residual charge of the HV capacitor 210 may be held in anticipation of a needed therapy.

In either case of terminating or completing charge adjustment at block 220, the ATP may be canceled at block 120 since the therapy may no longer be required (if the rate is slowing) or a different therapy may be needed (if the rate is accelerating). Control module 80 returns to block 102 to analyze the cardiac signal for redetecting the tachyarrhythmia, which may have terminated, remained in the original VT or VF detection zone, or accelerated within the VT zone or from the VT zone to the VF zone. By redetecting the tachyarrhythmia, the most appropriate therapy for the accelerating rhythm may be delivered, and delivery of a potentially sub-optimal or unnecessary therapy is avoided.

Figure 9:
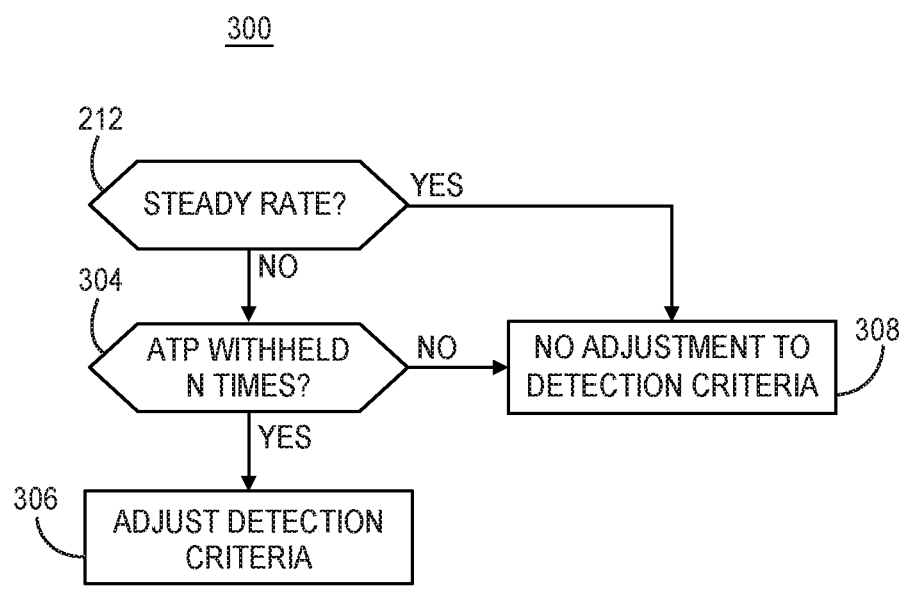
FIG. 9 is a flow chart of a method for adjusting tachyarrhythmia detection parameters in response to canceling an ATP therapy.

FIG. 9 is a flow chart 300 of a method for adjusting detection parameters in response to canceling an ATP therapy. The process of flow chart 300 provides additional steps that may be performed in response to determining a non-steady rate at block 212 of FIG. 8, shown again in FIG. 9. In response to determining that the rate is not steady, "no" branch of block 212, control module 80 may determine if ATP has been canceled a threshold number of times at block 304 due to a non-steady rate. In some examples, the determination at block 212 includes determining whether or not the rate is slowing or accelerating as described above.

If the rate is not steady and is slowing at block 212, the ATP is canceled as described in conjunction with FIG. 8. If ATP has not been withheld or canceled a threshold number of times (block 304), no adjustments to the tachyarrhythmia detection criteria are made at block 308. Control module 80 returns to monitoring the cardiac electrical signal after canceling ATP therapy, as described in conjunction with FIG. 8, to determine if the tachyarrhythmia is spontaneously terminating or if VT is still being detected using the same tachyarrhythmia detection criteria.

If ATP has been withheld or canceled a threshold number of times due to a slowing rate as determined at block 304, control module 80 may adjust the tachyarrhythmia detection criteria at block 306. For example, if monomorphic VT has been detected and ATP withheld due to a slowing rate of the monomorphic VT during HV capacitor preparation, the VT detection criteria may be adjusted to increase the time it takes for control module 80 to detect VT, e.g., by increasing the NID. For instance, if ATP has been withheld three times due to a slowing rate of a monomorphic VT, the NID used to detect VT may be increased at block 306.

In other examples, if the rate is determined to be non-steady and accelerating at block 212, ATP is withheld as described above, and control module 80 may advance to block 304 to determine if ATP has been withheld a threshold number of times in response to detecting an accelerating rate during HV capacitor preparation. If ATP has been withheld a threshold number of times due to an accelerating rate, detection criteria may be adjusted at block 306 to enable earlier detection of a shockable VT or VF rhythm, e.g., by adjusting the fast VT or VF detection interval and/or reducing the number of intervals required to detect a fast VT or VF as a shockable rhythm.

It is contemplated that tachyarrhythmia detection criteria may be adjusted at block 306 after ATP has been canceled a threshold number of times only due to rate slowing during HV capacitor preparation, only due to rate acceleration during HV capacitor preparation, or for both cases of rate slowing and for rate acceleration. It is understood that the detection criteria are adjusted differently for the two cases of a slowing rate and an accelerating rate. The threshold number of times for canceling ATP prior to adjusting detection criteria may be one or more times and may be different for rate slowing than for rate acceleration.

In the examples described above, ATP is delivered by HV therapy module 83 of extra-cardiovascular ICD 14. In other examples, some aspects of the techniques disclosed herein may be used to control ATP therapy delivery by LV therapy module 85 of ICD 14 or by a similar LV therapy module of an ICD or pacemaker coupled to one or more transvenous leads carrying endocardial electrodes, an ICD or pacemaker coupled to one or more leads carrying epicardial electrodes, or an intra-cardiac pacemaker configured to deliver ATP. The determination whether ATP delivery criteria are met after detecting ventricular tachyarrhythmia may be performed to enable a delayed ATP to be canceled when the detected tachyarrhythmia is determined to self-terminate or has a non-steady rate.

FIG. 10 is a schematic diagram of one example of a transvenous ICD system 400 in which aspects disclosed herein for controlling ATP therapy may be implemented. The IMD system 400 of FIG. 10 includes an ICD 410 coupled to a patient's heart 402 via transvenous electrical leads 406, 411, and 416. ICD 410 includes a connector block 412 that may be configured to receive the proximal ends of a right ventricular (RV) lead 416, a right atrial (RA) lead 411 and a coronary sinus (CS) lead 406, which are advanced transvenously for positioning electrodes for sensing and stimulation in three or all four heart chambers.

RV lead 416 is positioned such that its distal end is in the right ventricle for sensing RV cardiac signals and delivering pacing or shocking pulses in the right ventricle. For these purposes, RV lead 416 is equipped with pacing and sensing electrodes shown as a ring electrode 430 and a tip electrode 428. In some examples, tip electrode 428 is an extendable helix electrode mounted retractably within an electrode head 429. RV lead 416 is further shown to carry defibrillation electrodes 424 and 426, which may be elongated coil electrodes used to deliver high voltage CV/DF pulses. Defibrillation electrode 424 may be referred to herein as the "RV defibrillation electrode" or "RV coil electrode" because it may be carried along RV lead 416 such that it is positioned substantially within the right ventricle when distal pacing and sensing electrodes 428 and 430 are positioned for pacing and sensing in the right ventricle. Defibrillation electrode 426 may be referred to herein as a "superior vena cava (SVC) defibrillation electrode" or "SVC coil electrode" because it may be carried along RV lead 416 such that it is positioned at least partially along the SVC when the distal end of RV lead 416 is advanced within the right ventricle.

Each of electrodes 424, 426, 428 and 430 are connected to a respective insulated conductors extending within the body of lead 416. The proximal end of the insulated conductors are coupled to corresponding connectors carried by proximal lead connector 414, e.g., a DF-4 connector, at the proximal end of lead 416 for providing electrical connection to ICD 410. It is understood that although ICD 410 is illustrated in FIG. 10 as a multi-chamber device coupled to RA lead 411 and CS lead 406 in addition to RV lead 416, ICD 410 may be configured as a single chamber device coupled only to RV lead 416 and may be configured to perform the techniques disclosed herein using electrodes 424, 426, 428 and/or 430 (and in some examples housing 415) for receiving cardiac electrical signals for delivering electrical stimulation therapy, including ATP therapy.

RA lead 411 is positioned such that its distal end is in the vicinity of the right atrium and the superior vena cava. Lead 411 is equipped with pacing and sensing electrodes 417 and 421 shown as a tip electrode 417, which may be an extendable helix electrode mounted retractably within electrode head 419, and a ring electrode 421 spaced proximally from tip electrode 417. The electrodes 417 and 421 provide sensing and pacing in the right atrium and are each connected to a respective insulated conductor with the body of RA lead 411. Each insulated conductor is coupled at its proximal end to connector carried by proximal lead connector 413.

CS lead 406 is advanced within the vasculature of the left side of the heart via the coronary sinus and a cardiac vein 418. CS lead 406 is shown in the embodiment of FIG. 10 as having one or more electrodes 408 that may be used in combination with either RV coil electrode 420 or the SVC coil electrode 423 for delivering electrical shocks for cardioversion and defibrillation therapies. In other examples, coronary sinus lead 406 may also be equipped with one or more electrodes 408 for use in delivering pacing and/or for sensing cardiac electrical signals in the left chambers of the heart, i.e., the left ventricle and/or the left atrium. The one or more electrodes 408 are coupled to respective insulated conductors within the body of CS lead 406, which provides connection to the proximal lead connector 404.

The RA pacing and sensing electrodes 417 and 421 and the RV pacing and sensing electrodes 428 and 430 may be used as bipolar pairs, commonly referred to as a "tip-to-ring" configuration for sensing cardiac electrical signals and delivering low voltage pacing pulses, e.g., for ATP delivery following tachyarrhythmia detection as described herein. Further, RV tip electrode 428 may be selected with a coil electrode 424 or 426 to be used as an integrated bipolar pair, commonly referred to as a "tip-to-coil" configuration for sensing cardiac electrical signals. ICD 410 may, for example, select one or more sensing electrode vectors including a tip-to-ring sensing vector between electrodes 428 and 430 and a tip-to-coil sensing vector, e.g., between RV tip electrode 428 and SVC coil electrode 426, between RV tip electrode 428 and RV coil electrode 424, between RV ring electrode 430 and SVC coil electrode 426 or between RV ring electrode 430 and RV coil electrode 424 In some cases, any of electrodes 408, 417, 421, 424, 426, 428 or 430 may be selected by ICD 410 in a unipolar sensing configuration with the ICD housing 415 serving as the indifferent electrode, commonly referred to as the "can" or "case" electrode. It is recognized that numerous sensing and electrical stimulation electrode vectors may be available using the various electrodes carried by one or more of leads 406, 415 and 416 coupled to ICD 410, and ICD 410 may be configured to selectively couple one or more sensing electrode vectors to sensing circuitry enclosed by housing 415, e.g., sensing circuitry including one or more amplifiers, filters, rectifiers, comparators, sense amplifiers, analog-to-digital convertors and/or other circuitry configured to acquire a cardiac electrical signal for use in detecting cardiac arrhythmias, as generally described above in conjunction with FIG. 5.

Housing 415 encloses internal circuitry generally corresponding to the various modules and components described in conjunction with FIG. 5 for sensing cardiac signals, detecting tachyarrhythmia, and controlling therapy delivery. ICD 410 may be configured to detect atrial tachyarrhythmia and ventricular tachyarrhythmia and may be capable of delivering both atrial ATP and ventricular ATP. As such, the methods disclosed herein for delaying an ATP therapy after tachyarrhythmia detection and determining if ATP delivery criteria are met may be applied to atrial tachyarrhythmia detection and atrial ATP.

In some examples, the ICD housing 415 may serve as a subcutaneous defibrillation electrode in combination with one or more of the coil electrodes 424 or 426 for delivering CV/DF shocks. It is recognized that alternative lead systems may be substituted for the three lead system illustrated in FIG. 10. While a particular multi-chamber ICD and transvenous lead system 400 is illustrated in FIG. 10, methodologies described herein for detecting tachyarrhythmia and controlling ATP delivery based on ATP delivery criteria may adapted for use with any single chamber, dual chamber, or multi-chamber transvenous ICD or pacemaker system.

FIG. 11A is a schematic diagram of an implantable medical device system 500 that includes extra-cardiovascular ICD 14 coupled to extra-cardiovascular lead 16 extending in a substernal position, as shown in FIG. 2A, and an intra-cardiac pacemaker 512. In some examples, intra-cardiac pacemaker 512 may be configured to deliver cardiac pacing pulses, including ATP pulses, via housing-based electrodes 514 and 516. Intra-cardiac pacemaker 512 may be configured to detect ventricular tachyarrhythmia and deliver ATP. As such, intra-cardiac pacemaker 512 may include a sensing module, control module and therapy delivery module having a LV therapy module, which may generally correspond to LV therapy module 85 described in conjunction with FIG. 5. The control module may be configured to detect tachyarrhythmia from cardiac signals received by the sensing module in the manner described above in conjunction with FIG. 5. The control module may be configured to confirm that ATP delivery criteria are met before controlling the LV therapy delivery module to deliver ATP pulses. Intra-cardiac pacemaker 512 may generally correspond to the intra-cardiac pacemaker disclosed in U.S. Pat. No. 9,468,766 (Sheldon, et al.), incorporated herein by reference in its entirety. In some examples, ICD 14 may be omitted from system 500 such that intra-cardiac pacemaker 512 is provided for detecting cardiac rhythms and delivering cardiac pacing as needed, including ATP therapy using the techniques disclosed herein.

ICD 14 may be included in system 500 to provide high voltage cardioversion/defibrillation therapies as needed. In some examples, ICD 14 performs tachyarrhythmia detection, and pacemaker 512 may be a triggered pacemaker that is configured to receive a trigger signal from ICD 14 for controlling the timing of ATP pulses. In this case, pacemaker 512 may or may not be configured to detect tachyarrhythmia. ICD 14 may detect tachyarrhythmia and generate a trigger signal that is passed to intra-cardiac pacemaker 512 to control the timing of ATP pulses delivered by intra-cardiac pacemaker 512. In some examples, the trigger signal is passed directly from ICD 14 to pacemaker 512, e.g., using wireless telemetry signals or tissue conductance communication.

In other examples, as shown in FIG. 11B, IMD system 500 includes a trigger signal emitting device 520. Trigger signal emitting device 520 may be coupled to ICD 14 via a control signal line 522 for receiving a control signal from ICD 14. The control signal causes trigger signal emitting device 520 to emit a trigger signal that is received by intra-cardiac pacemaker 512. The trigger signal may be a tissue conductance communication signal, an acoustical signal, an optical signal or other wireless signal. Upon receiving a trigger signal, pacemaker 512 is triggered to deliver one or more pacing pulses. While trigger signal emitting device 520 is shown as a separate device coupled to ICD 14 via a control signal line 522, trigger signal emitting device 520 may be a wireless device configured to receive wireless control signals from ICD 14 or may be incorporated within ICD housing 15. Implantable medical device system 500 may generally correspond to any of the triggered pacing systems disclosed in pending U.S. Pat. No. 9,669,224 (Carney, et al.), incorporated herein by reference in its entirety.

Figure 12:
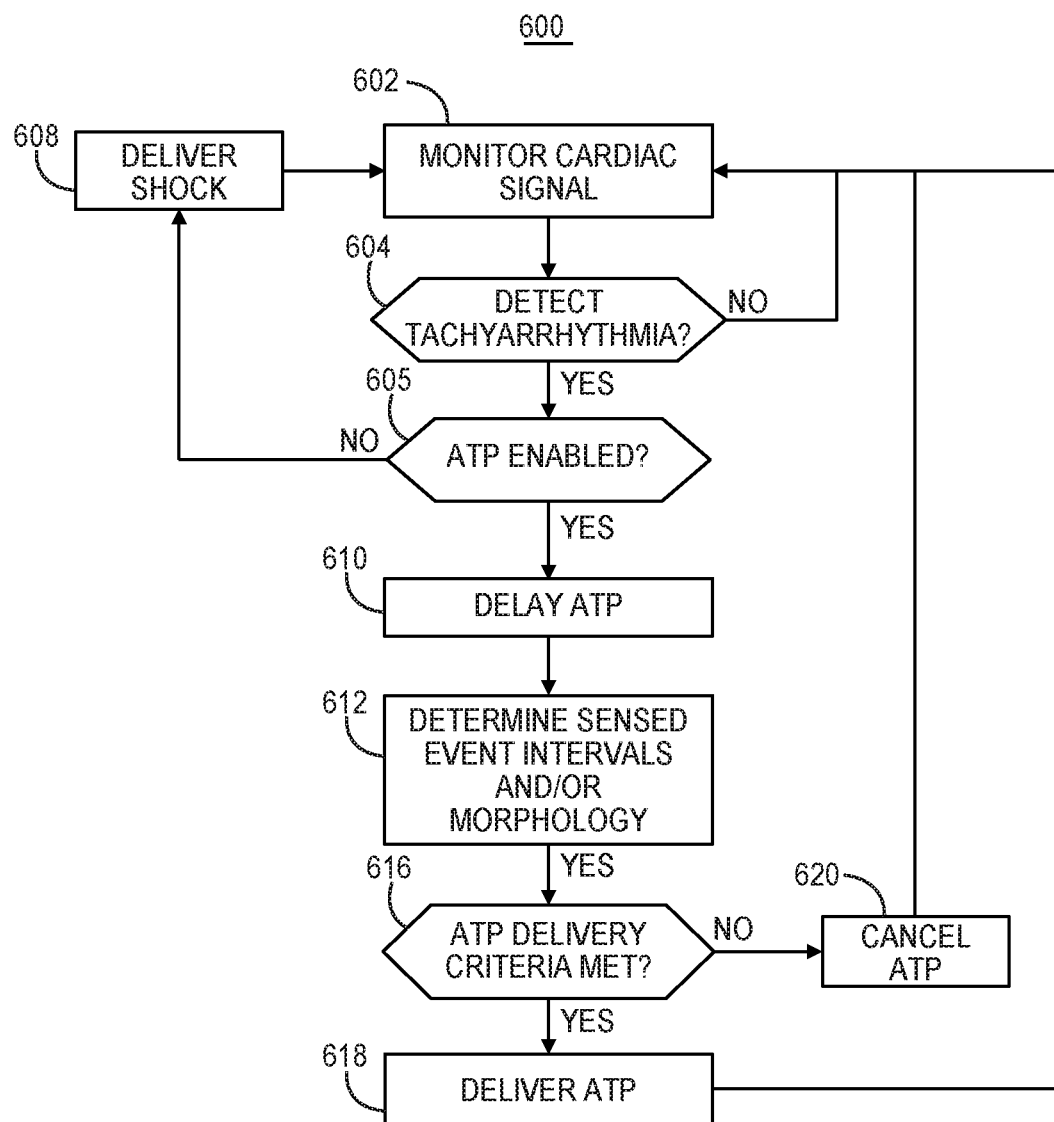
FIG. 12 is a flow chart of a method for controlling ATP therapy by an implantable medical device system according to another example.

FIG. 12 is a flow chart 600 of a method for controlling ATP therapy by an implantable medical device system according to another example. In various examples, the method of flow chart 600 may be performed by ICD 14 of FIGS. 1A-2C and FIGS. 11A and 11B, by ICD 410 of FIG. 10, by the intracardiac pacemaker 512 of FIG. 11A or 11B, or by a combination of ICD 14 and pacemaker 512 in the system 500 of FIGS. 11A and 11B. In these examples, either a HV therapy module 83 or a LV therapy module 85 may be used to deliver the ATP therapy, e.g., HV therapy module 83 or LV therapy module 85 shown in FIG. 5. A LV therapy module 85 may include one or more holding capacitors having a lower capacitance and a lower voltage rating than HV capacitor 210 of HV therapy module 83 since the LV therapy module 85 included in the IMD system for delivering ATP pulses is not configured to generate high voltage CV/DF shock pulses. The maximum voltage amplitude of a pacing pulse generated by the LV therapy module 85 may be 8 to 10 V.

In these examples, adjustment of the HV capacitor charge to the pacing voltage amplitude may not be required. The time to charge a LV therapy module holding capacitor is generally minimal such that an ATP pulse can be delivered at an ATP pacing interval following the tachyarrhythmia detection. However, an ICD system operating according to the techniques disclosed herein delays an enabled ATP therapy and determines if ATP delivery criteria are met during the ATP therapy delay, even if the therapy delivery module is ready to deliver the ATP therapy sooner than the ATP therapy delay period. This ATP therapy delay may allow the detected tachyarrhythmia to self-terminate, without requiring a therapy.

At block 602, cardiac electrical signal(s) are monitored for detecting a tachyarrhythmia using the techniques described above or in any of the incorporated references. The illustrative examples described herein generally relate to detecting ventricular tachyarrhythmia and delivering ventricular ATP. It is recognized, however, that the method of FIG. 12 and other methods disclosed herein may correspond to detecting atrial tachyarrhythmia and controlling atrial ATP therapy delivery, e.g., using system 400 of FIG. 10 or intra-cardiac pacemaker 512 of FIG. 11B positioned in an atrial chamber. If tachyarrhythmia is detected at block 604, control module 80 determines if ATP therapy is enabled for the detected tachyarrhythmia according to programmed therapies stored in memory 82. If ATP is not enabled, control module 80 may control the therapy delivery module 84 to deliver a shock therapy at block 608 when cardioversion/defibrillation shock capabilities are included.

If ATP is enabled at block 605, control module 80 delays the enabled ATP therapy at block 610. In IMD system 10 or 500, ICD 14 may be programmed to deliver ATP using the HV therapy module 83. Control module 80 may wait before delivering an enabled ATP therapy after tachyarrhythmia detection by controlling the HV therapy module 83 to prepare the HV capacitor for delivering the ATP therapy, e.g., as described above in conjunction with FIGS. 7 and 8. The time required for adjusting the HV capacitor to within a tolerance of the pacing voltage amplitude may be the ATP therapy delay period, which may be a variable time period depending on the time required to adjust the HV capacitor charge.

In other examples, control module 80 may wait to deliver the ATP at block 610 for a predetermined number of sensed cardiac events, e.g., a predetermined number of sensed R-waves and/or P-waves, or a predetermined number of sensed cardiac event intervals, e.g. a predetermined number of RR intervals or PP intervals. In other examples, control module 80 may wait to deliver ATP for a predetermined delay period set as a fixed time interval, e.g., 1 second, 2 seconds, 3 seconds, 5 seconds or other predetermined time interval. In any of these examples, IMD system 10, 400 or 500 may be programmed to deliver the ATP from a LV therapy module, such as LV therapy module 85. Preparation of the HV capacitor may not be required during the ATP delay period.

During the ATP delay period, control module 80 may determine sensed event intervals and/or sensed event morphology at block 612. As described above in conjunction with FIGS. 7 and 8, RRIs may be determined and compared to ATP delivery criteria at block 616 by comparing the RRIs to a synchronization interval established by the control module 80. If a predetermined number, percentage or ratio of the RRIs determined during the ATP delay period are less than the synchronization interval, the ATP delivery criteria are met at block 616.

In other examples, the implantable medical device system employing the techniques of FIG. 12 may be configured to determine PP intervals, PR intervals, RP intervals or other sensed cardiac event intervals for determining if the ATP delivery criteria are met at block 616. For example, the transvenous ICD system of FIG. 10 may be configured to sense atrial signals from the RA lead 411 and use atrial signals in determining if ATP delivery criteria are met at block 616. The ATP delivery criteria may be directed to control delivery of atrial ATP and/or ventricular ATP. The tachyarrhythmia detected at block 604 may be a supraventricular tachyarrhythmia or a ventricular tachyarrhythmia. The enabled ATP therapy (block 605) may be atrial ATP and/or ventricular ATP.

If a supraventricular tachyarrhythmia is detected at block 604 and atrial ATP is enabled, the control module may determine PP intervals between consecutively sensed P-waves for comparison to a synchronization interval at block 616. If a ventricular tachyarrhythmia is detected at block 604, the control module may determine RR intervals, PR intervals, RP intervals, or a combination of RR, PR and/or RP intervals for comparison to criteria for delivering ATP at block 616. Such criteria may generally require that a predetermined percentage or portion of the sensed event intervals be less than a synchronization interval and/or within an interval range indicating a steady rate of the detected tachyarrhythmia. If PR and/or RP intervals are determined to be regular and stable, atrial ATP delivery criteria may be met but ventricular ATP delivery criteria may be unmet since regular PR or RP intervals may indicate supraventricular tachyarrhythmia.

In addition to or alternatively to determining cardiac sensed event intervals at block 612, it is contemplated that sensed event morphology features or metrics may be determined at block 612 during the ATP delay. Sensed event morphology and/or sensed event intervals may be compared to ATP delivery criteria at block 616. For example, if ventricular ATP therapy is enabled and ventricular tachyarrhythmia is detected at block 604, the morphology of sensed events during the ATP delay may be compared to each other or a morphology template determined prior to the tachyarrhythmia detection or during the tachyarrhythmia detection to determine if the morphology represents a non-changing morphology during the ATP delay and/or since tachyarrhythmia detection.

The ATP delay period may be a variable period that is terminated upon determining whether ATP delivery criteria are met. Alternatively, the ATP delay period may be terminated after a predetermined time interval, number of sensed events or event intervals, or upon completion of capacitor preparation for ATP delivery when the HV therapy module 83 is used for ATP delivery. If ATP delivery criteria are met, ATP is delivered at block 618. Delivery of ATP at block 618 includes synchronizing the first ATP pulse to the most recent sensed event that resulted in ATP delivery criteria being met or immediately following ATP delivery criteria being met. The first pulse may be delivered at an ATP interval that is based on one or more cardiac event intervals determined during the ATP delay or the one or more sensed event intervals that let up to the tachyarrhythmia detection at block 604. ATP pulses may be generated and delivered by the LV pacing circuit of the IMD system, e.g., LV therapy module 85 shown in FIG. 5 or an analogous LV therapy module included in ICD 410 of FIG. 10 or pacemaker 512 shown in FIG. 11A or 11B.

In the system of FIG. 11A or 11B, ATP pulses may be delivered by intra-cardiac pacemaker 512. Intra-cardiac pacemaker 512 may include a control module that is configured to detect the tachyarrhythmia, delay ATP and determine if the ATP delivery criteria are met. Alternatively, intra-cardiac pacemaker 512 may be configured to receive trigger signals from ICD 14 or a trigger signal emitting device 520 for triggering pacemaker 512 to deliver ATP pulses after ICD 14 determines that ATP delivery criteria are met. In still another example, ICD 14 may detect the tachyarrhythmia and transmit a trigger signal to pacemaker 512, directly or via trigger signal emitting device 520, to cause pacemaker 512 to initiate an ATP therapy delay period and determine if ATP delivery criteria are met for making the decision of whether to deliver or cancel ATP after receiving the trigger signal from ICD 14.

If the ATP delivery criteria are not met at block 616, the delayed ATP therapy is canceled at block 620. After delivering or canceling the ATP, the control module returns to block 602 to continue monitoring the cardiac signal. As such, an IMD system configured to execute an ATP therapy delay period and ATP delivery confirmation based on ATP delivery criteria applied to a cardiac signal acquired during the ATP therapy delay period may be implemented in an IMD system that includes one or more implantable devices. The functions of detecting a tachyarrhythmia, starting an ATP therapy delay period, determining if ATP delivery criteria are met, and delivering (or canceling) the ATP therapy may be performed by a single device or distributed across more than one implantable medical device included in the IMD system.

Figure 13:
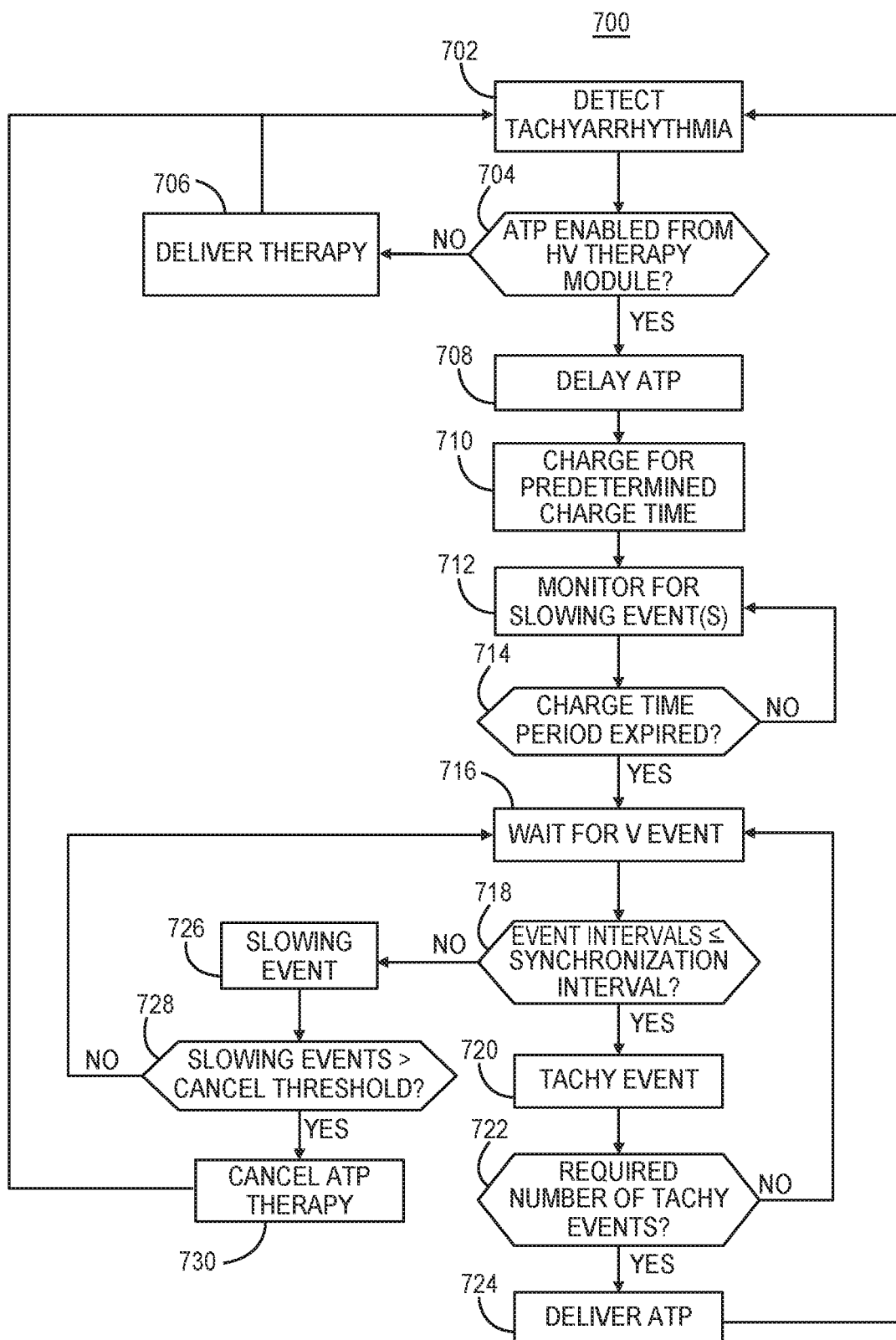
FIG. 13 is a flow chart of a method for controlling ATP therapy by an implantable medical device system according to another example.

FIG. 13 is a flow chart 700 of a method for controlling ATP therapy according to yet another example. Upon detecting a tachyarrhythmia at block 702, control module 80 may determine if ATP is enabled for delivery from the HV therapy module 83 at block 704. If not, control module 80 may deliver therapy at block 706 according to a programmed menu of therapies, which may include ATP delivered from the LV therapy module 85 and/or a shock therapy from the HV therapy module 83. ATP may be delivered from the LV therapy module 85 at block 706 without an ATP delay period. If ATP therapy is not enabled for the detected tachyarrhythmia, e.g., according to a programmed sequence of therapies, a CV/DF shock may be delivered at block 706.

In some cases, a maximum number of delayed ATP therapies may have been canceled due to ATP delivery criteria not being reached during an ATP delay period. If ATP is enabled to be delivered from the HV therapy module 83, but ATP has been canceled a maximum number of times, control module 80 may advance to deliver the next therapy at block 706, e.g., a shock therapy.

If ATP therapy is enabled for delivery from the HV therapy module 83 and a maximum number of canceled ATP therapies has not been reached, control module 80 starts the ATP delay period at block 708 and starts charging the HV capacitor at block 710. In this example, charging of the HV capacitor is performed for a predetermined charge time period. In some cases, the HV capacitor may reach a programmed ATP pacing pulse amplitude prior to the expiration of the predetermined charge time period but is held at the programmed pacing pulse amplitude for the ATP delay period. In one example, the capacitor charge time period is one second. In other examples, the capacitor charge time period may be more than one second. The capacitor charge time period may be selected to be at least long enough for the HV capacitor to be charged to the programmed pacing voltage amplitude for ATP therapy delivery.

During the ATP delay period, control module 80 may monitor for slowing events at block 712. A slowing event may be an RRI that is greater than the synchronization interval (established according to any of the techniques described above), a delivered ventricular pacing pulse or an expired ventricular pacing escape interval, e.g., during an OVO pacing mode. If a slowing event occurs during the capacitor charge time period, the slowing event may be counted by control module 80, but charging of the HV capacitor and maintenance of the HV capacitor charge at the pacing voltage amplitude continues for the predetermined fixed charge time period.

Upon expiration of the capacitor charge time period at block 714, the control module 80 waits for the next ventricular event at block 716. If the earliest ventricular event after the predetermined charge time period expires is a sensed R-wave, the RRI ending with the sensed R-wave is compared to the synchronization interval at block 718. If the RRI is less than or equal to the synchronization interval, the ventricular event is classified as a tachyarrhythmia event at block 720.

Control module 80 determines if a required number of tachyarrhythmia events have been detected at block 722, after the charge time period expired. In one example, only a single tachyarrhythmia event after the charge time period expires is required for ATP delivery criteria to be met. ATP is delivered from the HV therapy module 83 at block 724, synchronized to the first sensed R-wave after the charge time period expires. In other examples, two or more tachyarrhythmia events, e.g., two or more R-waves occurring at RRIs that are less than the synchronization interval, are required in order for ATP delivery criteria to be met before delivering ATP at block 724. If more than one tachyarrhythmia events are required for delivering the delayed ATP, the process returns to block 716 to wait for the next V event.

If the first ventricular event after the charge time period expires is a sensed R-wave occurring at an RRI that is greater than the synchronization interval, "no" branch of block 718, the event is classified as a slowing event at block 726. In some instances, a pacing escape interval may expire after the charge time period expires with no sensed R-wave. In this case, the first V event at block 716 may be a delivered ventricular pacing pulse. The ventricular event interval, an expired pacing escape interval, is greater than the synchronization interval at block 718, and a slowing event is detected at block 726. In an OVO pacing mode, no ventricular pacing pulse may be delivered at the expiration of a ventricular pacing escape interval but the expired pacing escape interval may be treated as an event interval that is greater than the synchronization interval and be detected as a slowing event at block 726.

Control module 80 determines at block 728 if a threshold number of slowing events have been counted since the ATP delay period was started. In some examples, control module 80 cancels the ATP therapy at block 730 in response to a single slowing event after the charge time period expires. In other examples, at least two slowing events are required at block 728 in order to cancel the ATP therapy at block 730. One or more slowing events may be detected during the charge time period with at least one slowing event after the charge time period expires. For instance, if at least one slowing event occurs during the charge time period and the first ventricular event after the charge time period expires is a slowing event, the ATP cancel threshold is reached at block 728. In other instances, if no slowing event occurs during the charge time period, two slowing events after expiration of the charge time period are required before canceling the ATP therapy at block 730.

An ATP therapy may be canceled multiple times before being delivered after at least one tachyarrhythmia event occurs after tachyarrhythmia detection and after the charge time period expires. After ATP is delivered at block 724, the tachyarrhythmia may be redetected at block 702. Control module 80 may advance to the next therapy in a sequence of programmed therapies enabled for treating the detected tachyarrhythmia if the tachyarrhythmia is redetected after the first therapy is delivered. The next therapy may be a second attempt of the same ATP sequence, a different ATP sequence, or a shock therapy. If the next therapy attempted after the tachyarrhythmia episode is redetected is the same or a different ATP therapy sequence using the HV therapy module 83, the method of FIG. 13 may be repeated to deliver the next ATP therapy after an ATP delay period as long as the threshold number of slowing events is not reached during the ATP delay period. A maximum number of canceled ATP therapies may be allowed. If the maximum number of canceled ATP therapies is reached, a CV/DF shock may be delivered at block 705 upon redetection of the tachyarrhythmia episode at block 702.

In the example of FIG. 13, ATP therapy enabled from the HV therapy module 83 is delayed by starting an ATP delay period, starting a fixed HV capacitor charge time, and verifying that at least the first sensed cardiac event after the fixed HV capacitor charge time is a tachyarrhythmia event. The ATP therapy delay period is terminated and the delayed ATP therapy is delivered in response to a threshold number, e.g., one or more, tachyarrhythmia events being detected after the fixed HV capacitor charge time expires. The ATP therapy delay period may be terminated and the delayed ATP therapy may be canceled in response to a threshold number, e.g., two or more, slowing events being detected during and/or after the fixed HV capacitor charge time expires. A slowing event is detected in response to each RRI greater than an established synchronization interval and in response to each expired ventricular pacing escape interval that occurs during the fixed capacitor charge time and/or after the fixed capacitor charge time expires.

Thus, an IMD system and method for controlling and delivering ATP therapy have been presented in the foregoing description with reference to specific embodiments. In other examples, various methods described herein may include steps performed in a different order or combination than the illustrative examples shown and described herein. It is appreciated that various modifications to the referenced embodiments may be made without departing from the scope of the disclosure and the following claims.

The invention claimed is:

1. An implantable medical device system comprising:
a sensing module configured to receive a cardiac electrical signal from a patient's heart via a sensing electrode vector and sense cardiac events from the cardiac electrical signal;
a therapy delivery module configured to generate pulses for delivering an anti-tachycardia pacing (ATP) therapy to the patient's heart via a pacing electrode vector;
wherein the therapy delivery module comprises a high voltage therapy module comprising:
a high voltage capacitor chargeable to a shock voltage amplitude; and
a high voltage charging circuit configured to charge the first capacitor to the shock voltage amplitude for delivering a cardioversion/defibrillation shock pulse; and
a control module coupled to the sensing module and the therapy delivery module and configured to:
detect a tachyarrhythmia from the cardiac electrical signal;
start an ATP therapy delay period to delay the ATP therapy in response to detecting the tachyarrhythmia;
in response to detecting the tachyarrhythmia, control the high voltage therapy module to adjust a charge of the high voltage capacitor to a pacing voltage amplitude during the ATP therapy delay period, the pacing voltage amplitude less than the shock voltage amplitude;
determine whether ATP delivery criteria are satisfied based on the cardiac electrical signal received by the sensing module during the ATP therapy delay period;
control the therapy delivery module to deliver the delayed ATP therapy in response to the ATP delivery criteria being satisfied; and
cancel the delayed ATP therapy in response to the ATP delivery criteria not being satisfied.

2. The system of claim 1, wherein the control module is configured to determine whether the ATP delivery criteria are satisfied by:
determining sensed cardiac event intervals during the ATP therapy delay period, each sensed cardiac event interval being determined as a time interval between a pair of consecutively sensed cardiac events sensed by the sensing module;
comparing the sensed cardiac event intervals determined during the ATP therapy delay period to a synchronization interval; and
determining that the ATP delivery criteria are satisfied in response to a threshold number of the sensed cardiac event intervals determined during the ATP therapy delay period being less than the synchronization interval.

3. The system of claim 2, wherein the control module is further configured to:
detect the tachyarrhythmia in response to a predetermined number of sensed event intervals determined from the cardiac electrical signal being less than a tachyarrhythmia detection interval; and
establish the synchronization interval based on at least one of the tachyarrhythmia detection interval and/or at least a portion of the predetermined number of sensed event intervals less than the tachyarrhythmia detection interval.

4. The system of claim 2, wherein the control module is further configured to determine that the ATP delivery criteria are met by:
detecting a steady rate of the detected tachyarrhythmia during the ATP therapy delay period in response to sensed cardiac event intervals determined during the ATP therapy delay period being within an interval range.

5. The system of claim 1, wherein:
the control module is configured to:
determine if the capacitor charge is within a tolerance of the pacing voltage amplitude; and
in response to determining that the capacitor charge is within the tolerance of the pacing voltage amplitude, determine if the ATP delivery criteria are met.

6. The system of claim 5, wherein the control module is configured to adjust the high voltage capacitor charge to within the tolerance of the pacing voltage amplitude by dumping a portion of a residual charge stored on the high voltage capacitor through a non-therapeutic load.

7. The system of claim 5, wherein the control module is configured to adjust the high voltage capacitor charge to within the tolerance of the pacing voltage amplitude by controlling the high voltage charging circuit to charge the high voltage capacitor.

8. The system of claim 5, wherein the control module is further configured to:
determine sensed cardiac event intervals during the ATP therapy delay period, each sensed cardiac event interval being determined as a time interval between a pair of consecutively sensed cardiac events sensed by the sensing module;
detect a non-steady rate of the detected tachyarrhythmia during the ATP therapy delay period by determining that the sensed cardiac event intervals do not remain within an interval range during the ATP delay period;
terminate the adjusting of the capacitor charge in response to the non-steady rate of the detected tachyarrhythmia; and
cancel the ATP therapy in response to detecting the non-steady rate.

9. The system of claim 5, wherein the control module is configured to control the high voltage therapy module to hold the high voltage capacitor charge at the pacing voltage amplitude in response to the ATP delivery criteria not being met.

10. The system of claim 9, wherein the control module is further configured to:
redetect the tachyarrhythmia after canceling the ATP therapy;
determine that the redetected tachyarrhythmia has accelerated; and
control the high voltage therapy module to:
charge the high voltage capacitor from the pacing voltage amplitude to the shock voltage amplitude in response to the tachyarrhythmia being accelerated; and
deliver a cardioversion/defibrillation shock pulse having the shock voltage amplitude.

11. The system of claim 5, wherein the control module is further configured to:
compare a charge of the high voltage capacitor to charge adjustment criteria in response to detecting the tachyarrhythmia; and
cancel the ATP therapy in response to the charge adjustment criteria not being met.

12. The system of claim 1, wherein the control module is further configured to:
detect a non-steady rate of the detected tachyarrhythmia during the ATP therapy delay period;

cancel the delayed ATP therapy in response to the detected non-steady rate;
determine that ATP therapy has been canceled a threshold number of times; and
adjust tachyarrhythmia detection criteria used for detecting the tachyarrhythmia in response to the ATP therapy being canceled the threshold number of times.

13. The system of claim 1, wherein the control module is configured to delay the ATP therapy for one of a predetermined time interval, a predetermined number of sensed cardiac events, or capacitor charge time.

14. The system of claim 1 further comprising an intra-cardiac pacemaker including the therapy delivery module;
wherein the control module controls the intra-cardiac pacemaker to deliver the ATP therapy in response to the ATP therapy delivery criteria being satisfied.

15. The system of claim 1, comprising a housing enclosing the sensing module, the therapy delivery module and the control module, the housing comprising a connector block for receiving an extra-cardiovascular lead carrying at least one electrode of the pacing electrode vector.

16. The system of claim 1, comprising a housing enclosing the sensing module, the therapy delivery module and the control module, the housing comprising a connector block for receiving a transvenous lead carrying at least one electrode of the pacing electrode vector.

17. The system of claim 1, wherein the control module is further configured to:
charge a capacitor of the therapy delivery module during the ATP therapy delay period during a fixed capacitor charge time period;
classify a cardiac event sensed by the sensing module after the fixed capacitor charge time period as one of a slowing event or a tachyarrhythmia event;
determine that the ATP delivery criteria are satisfied in response to the cardiac event being classified as a tachyarrhythmia event; and
determine that the ATP delivery criteria are not satisfied in response to the cardiac event being classified as a slowing event.

18. The system of claim 17, wherein the control module is configured to detect a slowing event during the ATP therapy delay period in response to at least one of:
a cardiac event sensed by the sensing module at a cardiac event interval that is greater than a synchronization interval, or
an expired cardiac pacing escape interval.

19. The system of claim 18, wherein the control module is further configured to determine that the ATP delivery criteria are not satisfied in response to detecting a threshold number of slowing events during the ATP therapy delay period.

20. A method comprising:
detecting a tachyarrhythmia from a cardiac electrical signal received from a patient's heart;
starting an anti-tachycardia pacing (ATP) therapy delay period to delay an ATP therapy in response to detecting the tachyarrhythmia;
adjusting a charge of a high voltage capacitor to a pacing voltage amplitude during the ATP therapy delay period, the high voltage capacitor chargeable to a shock voltage amplitude for delivering a cardioversion/defibrillation shock pulse, the pacing voltage amplitude less than the shock voltage amplitude;
determining whether ATP delivery criteria are satisfied based on the cardiac electrical signal received during the ATP therapy delay period;
delivering the delayed ATP therapy in response to the ATP delivery criteria being satisfied; and
canceling the delayed ATP therapy in response to the ATP delivery criteria not being satisfied.

21. The method of claim 20, wherein determining if the ATP delivery criteria are satisfied comprises:
determining sensed cardiac event intervals during the ATP therapy delay period, each sensed cardiac event interval being determined as a time interval between a pair of consecutively sensed cardiac events;
comparing the determined sensed cardiac event intervals to a synchronization interval; and
determining that the ATP delivery criteria are satisfied in response to a threshold number of the determined sensed cardiac event intervals being less than the synchronization interval.

22. The method of claim 21, further comprising:
detecting the tachyarrhythmia in response to a predetermined number of sensed event intervals determined from the cardiac electrical signal being less than a tachyarrhythmia detection interval; and
establishing the synchronization interval based on at least one of the tachyarrhythmia detection interval and/or at least a portion of the predetermined number of sensed event intervals less than the tachyarrhythmia detection interval.

23. The method of claim 21, wherein determining that the ATP delivery criteria are met further comprises:
detecting a steady rate of the detected tachyarrhythmia during the ATP therapy delay period in response to sensed cardiac event intervals determined during the ATP therapy delay period being within an interval range.

24. The method of claim 20, further comprising:
determining if the high voltage capacitor charge is within a tolerance of the pacing voltage amplitude; and
in response to the capacitor charge being adjusted to within the tolerance of the pacing voltage amplitude, determining if the ATP delivery criteria are met.

25. The method of claim 24, wherein adjusting the high voltage capacitor charge to within the tolerance of the pacing voltage amplitude comprises dumping a portion of a residual charge stored on the high voltage capacitor through a non-therapeutic load.

26. The method of claim 24, wherein adjusting the high voltage capacitor charge to within the tolerance of the pacing voltage amplitude comprises charging the high voltage capacitor.

27. The method of claim 24, further comprising:
determining sensed cardiac event intervals during the ATP therapy delay period, each sensed cardiac event interval being determined as a time interval between a pair of consecutively sensed cardiac events;
detecting a non-steady rate of the detected tachyarrhythmia during the ATP therapy delay period by determining that the sensed cardiac event intervals do not remain within an interval range during the ATP delay period;
terminating the adjusting of the capacitor charge in response to the non-steady rate of the detected tachyarrhythmia; and
canceling the ATP therapy in response to detecting the non-steady rate.

28. The method of claim 24, further comprising holding the high voltage capacitor charge at the pacing voltage amplitude in response to the ATP delivery criteria not being met.

29. The method of claim 28, further comprising:
redetecting the tachyarrhythmia after canceling the ATP therapy;
determining that the redetected tachyarrhythmia has accelerated;
charging the high voltage capacitor from the pacing voltage amplitude to the shock voltage amplitude in response to the tachyarrhythmia being accelerated; and
delivering a cardioversion/defibrillation shock pulse having the shock voltage amplitude.

30. The method of claim 24, further comprising:
comparing a charge of the high voltage capacitor to charge adjustment criteria in response to detecting the tachyarrhythmia; and
canceling the ATP therapy in response to the charge adjustment criteria not being met.

31. The method of claim 20, further comprising:
detecting a non-steady rate of the detected tachyarrhythmia during the ATP therapy delay period;
canceling the delayed ATP therapy in response to the rate of the detected tachyarrhythmia not being steady during the ATP delay period;
determining that ATP therapy has been canceled a threshold number of times; and
adjusting tachyarrhythmia detection criteria used for detecting the tachyarrhythmia in response to ATP therapy being canceled the threshold number of times.

32. The method of claim 20, further comprising delaying the ATP therapy for one of a predetermined time interval, a predetermined number of sensed cardiac events, or a capacitor charge time.

33. The method of claim 20, further comprising controlling an intra-cardiac pacemaker to deliver the ATP therapy in response to the ATP therapy delivery criteria being satisfied.

34. The method of claim 20, further comprising delivering the ATP therapy via at least one electrode carried by an extra-cardiovascular lead.

35. The method of claim 20, further comprising:
charging a capacitor of the therapy delivery module during the ATP therapy delay period during a fixed capacitor charge time period;
classifying a sensed cardiac event after the fixed capacitor charge time period as one of a slowing event or a tachyarrhythmia event; and
determining that the ATP delivery criteria are satisfied in response to the cardiac event being classified as a tachyarrhythmia event; and
determining that the ATP delivery criteria are not satisfied in response to the cardiac event being classified as a slowing event.

36. The method of claim 35, further comprising detecting a slowing event during the ATP therapy delay period in response to at least one of:
a sensed cardiac event interval that is greater than a synchronization interval, or
an expired cardiac pacing escape interval.

37. The method of claim 36, further comprising determining that the ATP delivery criteria are not satisfied in response to detecting a threshold number of slowing events during the ATP therapy delay period.

38. A non-transitory, computer-readable storage medium comprising a set of instructions which, when executed by a processor cause the processor to:
detect a tachyarrhythmia from a cardiac electrical signal received from a patient's heart;
start an anti-tachycardia pacing (ATP) therapy delay period to delay an ATP therapy in response to detecting the tachyarrhythmia;
adjust a charge of a high voltage capacitor to a pacing voltage amplitude during the ATP therapy delay period, the high voltage capacitor chargeable to a shock voltage amplitude for delivering a cardioversion/defibrillation shock pulse, the pacing voltage amplitude less than the shock voltage amplitude;
determine whether ATP delivery criteria are satisfied based on the cardiac electrical signal received during the ATP therapy delay period;
deliver the delayed ATP therapy in response to the ATP delivery criteria being satisfied; and
cancel the delayed ATP therapy in response to the ATP delivery criteria not being satisfied.

* * * * *